United States Patent [19]
Edwards et al.

[11] Patent Number: 6,126,657
[45] Date of Patent: *Oct. 3, 2000

[54] APPARATUS FOR TREATMENT OF AIR WAY OBSTRUCTIONS

[75] Inventors: Stuart D. Edwards, Portola Valley, Calif.; Ronald G. Lax, Palm City, Fla.

[73] Assignee: Somnus Medical Technologies, Inc., Sunnyvale, Calif.

[ * ] Notice: This patent is subject to a terminal disclaimer.

[21] Appl. No.: 08/895,785

[22] Filed: Jul. 17, 1997

Related U.S. Application Data

[63] Continuation-in-part of application No. 08/695,802, Aug. 12, 1996, Pat. No. 5,879,349, which is a continuation-in-part of application No. 08/651,800, May 22, 1996, Pat. No. 5,836,906, which is a continuation-in-part of application No. 08/642,053, May 3, 1996, Pat. No. 5,728,094, which is a continuation-in-part of application No. 08/606,195, Feb. 23, 1996, Pat. No. 5,707,349.

[51] Int. Cl.[7] .............................. A61B 18/18; A61N 1/30
[52] U.S. Cl. ................................................ 606/45; 604/21
[58] Field of Search .................. 606/29–52; 607/98–106; 604/19–21

[56] References Cited

U.S. PATENT DOCUMENTS

| | | |
|---|---|---|
| 1,798,902 | 3/1931 | Raney . |
| 3,901,241 | 8/1975 | Allen, Jr. .............................. 128/303.1 |
| 4,011,872 | 3/1977 | Komiya ............................... 128/303.14 |
| 4,196,724 | 4/1980 | Wirt et al. ................................. 128/136 |
| 4,411,266 | 10/1983 | Cosman ............................. 128/303.18 |
| 4,423,812 | 1/1984 | Sato ......................................... 206/387 |
| 4,532,924 | 8/1985 | Auth et al. .......................... 128/303.17 |
| 4,565,200 | 1/1986 | Cosman ................................... 128/642 |
| 4,901,737 | 2/1990 | Toone ....................................... 128/848 |
| 4,906,203 | 3/1990 | Margrave et al. ....................... 439/188 |
| 4,907,589 | 3/1990 | Cosman .................................... 606/34 |
| 4,943,290 | 7/1990 | Rexroth et al. ........................... 606/45 |
| 4,947,842 | 8/1990 | Marchosky et al. .................... 128/401 |

(List continued on next page.)

FOREIGN PATENT DOCUMENTS

| | | |
|---|---|---|
| 0 139 607 A1 | 5/1985 | European Pat. Off. . |
| 0 608 609 A2 | 8/1994 | European Pat. Off. . |
| 43 03 882 | 2/1995 | Germany . |
| 38 38 840 | 2/1997 | Germany . |
| 92/10142 | 6/1992 | WIPO . |
| 93/08755 | 5/1993 | WIPO . |
| 94/10925 | 5/1994 | WIPO . |
| 94/26178 | 11/1994 | WIPO . |
| WO 95/13752 | 5/1995 | WIPO ............................ A61B 17/39 |
| 95/18575 | 7/1995 | WIPO . |
| 95/19142 | 7/1995 | WIPO . |
| 95/25472 | 9/1995 | WIPO . |
| WO 96/18349 | 6/1996 | WIPO ............................ A61B 17/39 |
| 96/29946 | 10/1996 | WIPO . |
| WO 97/06738 | 2/1997 | WIPO ............................ A61B 17/39 |
| WO 97/06741 | 2/1997 | WIPO ............................ A61B 17/39 |

OTHER PUBLICATIONS

Kaneko, et al., *Physiological Laryngeal Pacemaker*, May 1985, Trans Am Soc Artif Intern Organs, vol. XXXI, pp. 293–296.

(List continued on next page.)

*Primary Examiner*—Sharon Kennedy
*Attorney, Agent, or Firm*—Wilson Sonsini Goodrich and Rosati

[57] ABSTRACT

An apparatus that reduces a volume of a selected site in an interior of the tongue includes a handpiece and an energy delivery device at least partially positioned in the interior of the handpiece. The energy delivery device includes an energy delivery surface and is advanceable from the interior of the handpiece into the interior of the tongue. An energy delivery device advancement member is coupled to the energy delivery device and configured to advance the energy delivery device an advancement distance in the interior of the tongue. The advancement distance is sufficient for the energy delivery surface to deliver energy to the selected tissue site and reduce a volume of the selected site without damaging a main branch of the hypoglossal nerve. A cable is coupled to the energy delivery device.

42 Claims, 18 Drawing Sheets

U.S. PATENT DOCUMENTS

| | | | |
|---|---|---|---|
| 4,966,597 | 10/1990 | Cosman | 606/50 |
| 4,976,711 | 12/1990 | Parins et al. | 606/48 |
| 5,046,512 | 9/1991 | Murchie | 128/848 |
| 5,057,107 | 10/1991 | Parins et al. | 606/48 |
| 5,078,717 | 1/1992 | Parins et al. | 606/48 |
| 5,083,565 | 1/1992 | Parins | 128/642 |
| 5,094,233 | 3/1992 | Brennan | 602/6 |
| 5,100,423 | 3/1992 | Fearnot | 606/159 |
| 5,122,137 | 6/1992 | Lennox | 606/40 |
| 5,125,928 | 6/1992 | Parins et al. | 606/48 |
| 5,190,541 | 3/1993 | Abele et al. | 606/46 |
| 5,197,963 | 3/1993 | Parins | 606/46 |
| 5,197,964 | 3/1993 | Parins | 606/46 |
| 5,215,103 | 6/1993 | Desai | 128/784 |
| 5,256,138 | 10/1993 | Burek et al. | 606/42 |
| 5,257,451 | 11/1993 | Edwards et al. | 29/825 |
| 5,275,162 | 1/1994 | Edwards et al. | 128/642 |
| 5,277,201 | 1/1994 | Stern | 607/98 |
| 5,281,216 | 1/1994 | Klicek | 606/42 |
| 5,281,217 | 1/1994 | Edwards et al. | 606/41 |
| 5,281,218 | 1/1994 | Imran | 606/41 |
| 5,290,286 | 3/1994 | Parins | 606/50 |
| 5,293,869 | 3/1994 | Edwards et al. | 128/642 |
| 5,309,910 | 5/1994 | Edwards et al. | 128/642 |
| 5,313,943 | 5/1994 | Houser et al. | 128/642 |
| 5,314,466 | 5/1994 | Stern et al. | 607/156 |
| 5,316,020 | 5/1994 | Truffer | 128/848 |
| 5,328,467 | 7/1994 | Edwards et al. | 604/95 |
| 5,334,196 | 8/1994 | Scott et al. | 606/138 |
| 5,348,554 | 9/1994 | Imran et al. | 606/41 |
| 5,363,861 | 11/1994 | Edwards et al. | 128/772 |
| 5,365,926 | 11/1994 | Desai | 128/642 |
| 5,365,945 | 11/1994 | Halstrom | 128/848 |
| 5,366,490 | 11/1994 | Edwards et al. | 607/99 |
| 5,368,557 | 11/1994 | Nita et al. | 604/22 |
| 5,368,592 | 11/1994 | Stern et al. | 606/33 |
| 5,370,675 | 12/1994 | Edwards et al. | 607/101 |
| 5,370,678 | 12/1994 | Edwards et al. | 607/101 |
| 5,383,876 | 1/1995 | Nardella | 606/49 |
| 5,383,917 | 1/1995 | Desai | 607/702 |
| 5,385,544 | 1/1995 | Edwards et al. | 604/22 |
| 5,397,339 | 3/1995 | Desai | 687/116 |
| 5,398,683 | 3/1995 | Edwards et al. | 128/642 |
| 5,401,272 | 3/1995 | Perkins | 606/15 |
| 5,403,311 | 4/1995 | Abele et al. | 606/49 |
| 5,409,453 | 4/1995 | Lundquist et al. | 604/22 |
| 5,421,819 | 6/1995 | Edwards et al. | 604/22 |
| 5,423,808 | 6/1995 | Edwards et al. | 606/34 |
| 5,423,811 | 6/1995 | Imran et al. | 606/41 |
| 5,423,812 | 6/1995 | Ellman et al. | 606/45 |
| 5,433,739 | 7/1995 | Sluijter et al. | 607/99 |
| 5,435,805 | 7/1995 | Edwards et al. | 604/22 |
| 5,441,499 | 8/1995 | Fritzsch | 606/45 |
| 5,456,662 | 10/1995 | Edwards et al. | 604/22 |
| 5,456,682 | 10/1995 | Edwards et al. | 606/31 |
| 5,458,596 | 10/1995 | Lax et al. | 606/31 |
| 5,458,597 | 10/1995 | Edwards et al. | 606/41 |
| 5,470,308 | 11/1995 | Edwards et al. | 604/22 |
| 5,471,982 | 12/1995 | Edwards et al. | 128/642 |
| 5,472,441 | 12/1995 | Edwards et al. | 606/41 |
| 5,484,400 | 1/1996 | Edwards et al. | 604/22 |
| 5,486,161 | 1/1996 | Lax et al. | 604/22 |
| 5,505,728 | 4/1996 | Ellman et al. | 606/39 |
| 5,505,730 | 4/1996 | Edwards | 606/41 |
| 5,507,743 | 4/1996 | Edwards et al. | 606/41 |
| 5,509,419 | 4/1996 | Edwards et al. | 128/642 |
| 5,514,130 | 5/1996 | Baker | 606/41 |
| 5,514,131 | 5/1996 | Edwards et al. | 606/45 |
| 5,520,684 | 5/1996 | Imran | 606/41 |
| 5,531,676 | 7/1996 | Edwards et al. | 604/22 |
| 5,531,677 | 7/1996 | Lundquist et al. | 604/22 |
| 5,536,240 | 7/1996 | Edwards et al. | 604/22 |
| 5,536,267 | 7/1996 | Edwards et al. | 606/41 |
| 5,540,655 | 7/1996 | Edwards et al. | 604/22 |
| 5,542,915 | 8/1996 | Edwards et al. | 604/22 |
| 5,542,916 | 8/1996 | Hirsch et al. | 604/22 |
| 5,545,161 | 8/1996 | Imran | 606/41 |
| 5,545,171 | 8/1996 | Sharkey et al. | 606/148 |
| 5,545,193 | 8/1996 | Fleischman et al. | 607/99 |
| 5,545,434 | 8/1996 | Huarng | 427/243 |
| 5,549,108 | 8/1996 | Edwards et al. | 128/642 |
| 5,549,644 | 8/1996 | Lundquist et al. | 604/22 |
| 5,554,110 | 9/1996 | Edwards et al. | 604/22 |
| 5,556,377 | 9/1996 | Rosen et al. | 604/22 |
| 5,558,672 | 9/1996 | Edwards et al. | 606/41 |
| 5,558,673 | 9/1996 | Edwards et al. | 606/41 |
| 5,599,345 | 2/1997 | Edwards et al. | 606/41 |
| 5,609,151 | 3/1997 | Mulier et al. | 128/642 |
| 5,624,439 | 4/1997 | Edwards et al. | 606/45 |
| 5,800,432 | 9/1998 | Swanson | 606/49 |

OTHER PUBLICATIONS

Mugica, et al. *Direct Diaphragm Stimulation*, Jan., 1987, PACE, vol. 10, pp. 252–256.

Mugica, et al. Neurostimulation: An Overview, Chapter 21, *Preliminary Test of a Muscular Diaphragm Pacing System on Human Patients*, 1985, pp. 263–279.

Nochomovitz, et al., *Electrical Activation of the Diaphragm*, Jun. 1988, Clinics in Chest Medicine, vol. 9, No. 2, pp. 349–358.

Prior, et al., *Treatment of Menorrhagia by Radiofrequency Heating*, 1991, Int. J. Hyperthermia, vol. 7, pp. 213–220.

Rice, et al., Endoscopic Paranasal Sinus Surgery, Chapter 5, *Functional Endoscopic Paranasal Sinus Surgery, The Technique of Messerklinger*, Raven Press, 1988, pp. 75–104.

Rice, et al., Endoscopic Paranasal Sinus Surgery, Chapter 6, *Total Endoscopic Sphenoetnmoidectomy, The Technique of Wigand*, Raven Press, 1988, pp. 105–125.

CONNECTOR SECTION

INTRODUCER SECTION

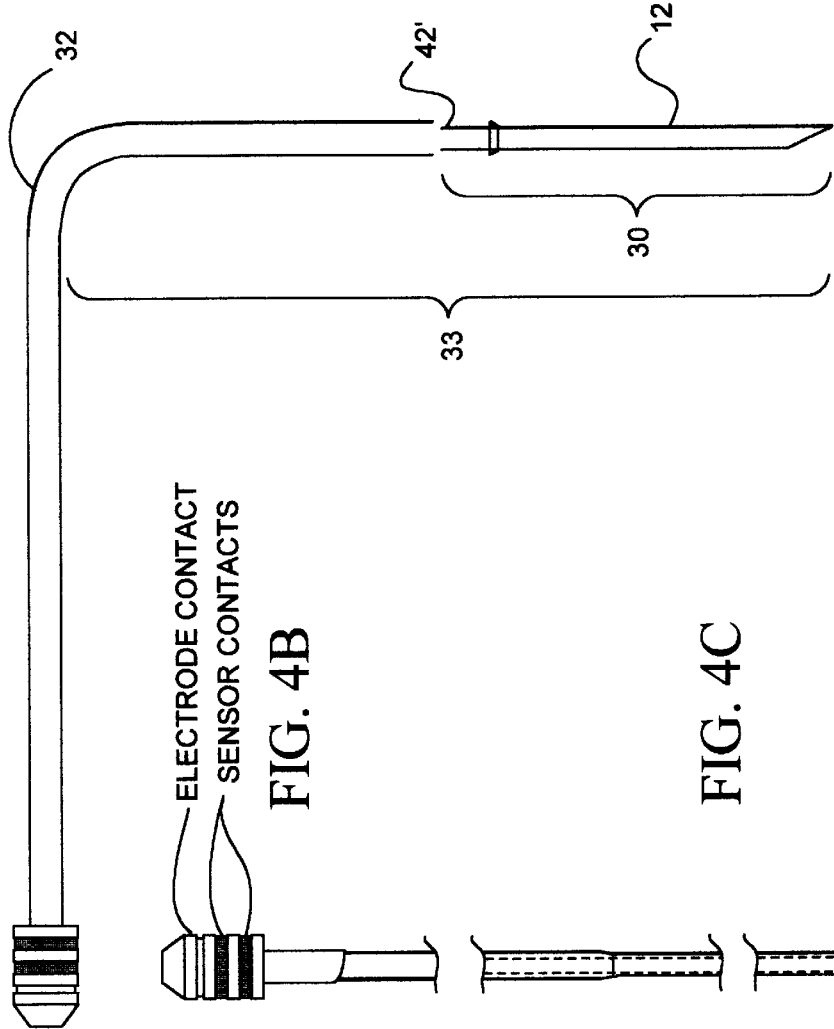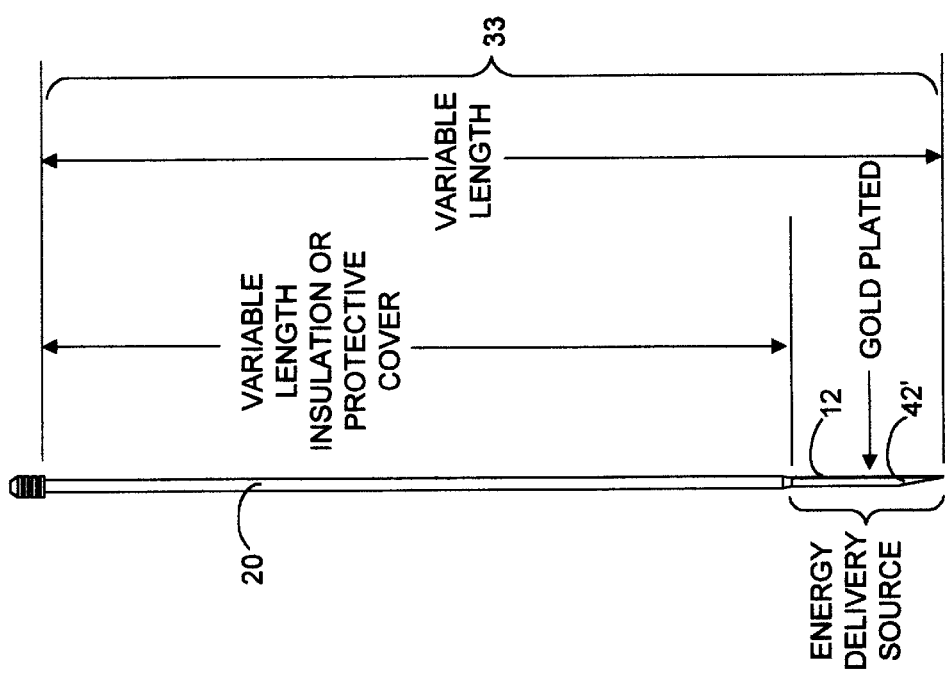

APPARATUS FOR TREATMENT OF AIR WAY OBSTRUCTIONS

CROSS-REFERENCE TO RELATED APPLICATIONS

This application is a continuation-in-part application of U.S. patent application Ser. No. 08/695,802 filed Aug. 12, 1995 now U.S. Pat. No. 5,879,349, which is a continuation-in-part of U.S. patent application Ser. No. 08/651,800, filed May 22, 1996 now U.S. Pat. No. 5,836,906, which is a continuation-in-part application of U.S. patent application Ser. No. 08/642,053, filed May 3, 1996 now U.S. Pat. No. 5,728,094, which is a continuation-in-part application of U.S. patent application Ser. No. 08/606,195, filed Feb. 23, 1996 now U.S. Pat. No. 5,707,349, which cross-references U.S. Pat. No. 5/674,191, having named inventors Stuart D. Edwards, Edward J. Gough and David L. Douglass, which is a continuation-in-part of U.S. Pat. No. 5,456,662, all incorporated by reference herein.

BACKGROUND OF THE INVENTION

1. Field of the Invention

This invention relates to an apparatus for the treatment of air way obstructions, and more particularly to an apparatus for reducing a volume of a selected site of an interior of the tongue, and more particularly to an apparatus for creating ablation at a selected site of an interior of the tongue without damaging a main branch of the hypoglossal nerve.

2. Description of Related Art

Sleep-apnea syndrome is a medical condition characterized by daytime hypersomnombulence, morning arm aches, intellectual deterioration, cardiac arrhythmias, snoring and thrashing during sleep. It is caused by frequent episodes of apnea during the patient's sleep. The syndrome is classically subdivided into two types. One type, termed "central sleep apnea syndrome", is characterized by repeated loss of respiratory effort. The second type, termed obstructive sleep apnea syndrome, is characterized by repeated apneic episodes during sleep resulting from obstruction of the patient's upper airway or that portion of the patient's respiratory tract which is cephalad to, and does not include, the larynx.

Treatment thus far includes various medical, surgical and physical measures. Medical measures include the use of medications such as protriptyline, medroxyprogesterone, acetazolamide, theophylline, nicotine and other medications in addition to avoidance of central nervous system depressants such as sedatives or alcohol. The medical measures above are sometimes helpful but are rarely completely effective. Further, the medications frequently have undesirable side effects.

Physical measures have included weight loss to open the airway, use of nasal CPAP and various tongue retaining devices. These devices may be partially effective but are cumbersome, uncomfortable and patients often will not continue to use these for prolonged periods of time. Weight loss may be effective but is rarely maintained by these patients.

In patients with central sleep apnea syndrome, phrenic nerve or diaphragmatic pacing has been used. Phrenic nerve or diaphragmatic pacing includes the use of electrical stimulation to regulate and control the patient's diaphragm which is innervated bilaterally by the phrenic nerves to assist or support ventilation. This pacing is disclosed in *Direct Diaphragm Stimulation* by J. Mugica et al. PACE vol. 10 January–Febuary 1987, Part II, *Preliminary Test of a Muscular Diaphragm Pacing System on Human Patients* by J. Mugica et al. from Neurostimulation: An Overview 1985 pp. 263–279 and *Electrical Activation of Respiration* by Nochomovitez IEEE Eng. in Medicine and Biology; June, 1993.

However, it was found that many of these patients also have some degree of obstructive sleep apnea which worsens when the inspiratory force is augmented by the pacer. The ventilation induced by the activation of the diaphragm also collapses the upper airway upon inspiration and draws the patient's tongue inferiorly down the throat choking the patient. These patients then require tracheostomies for adequate treatment.

A physiological laryngeal pacemaker as described in *Physiological Laryngeal Pacemaker* by F. Kaneko et al. from Trans Am Soc Artif Intern Organs 1985, senses volume displaced by the lungs and stimulates the appropriate nerve to open the patient's glottis to treat dyspnea. This apparatus is not effective for treatment of sleep apnea. The apparatus produces a signal proportional in the displaced air volume of the lungs and thereby the signal produced is too late to be used as an indicator for the treatment of sleep apnea. There is often no displaced air volume in sleep apnea due to obstruction.

Surgical interventions have included uvulopalatopharyngoplasty, tonsillectomy, tracheostomy, and surgery to correct severe retrognathia. One measure that is effective in obstructive sleep apnea is tracheostomy. However, this surgical intervention carries considerable morbidity and is aesthetically unacceptable to many patients. Other surgical procedures include pulling the tongue as forward as possible and surgically cutting and removing sections of the tongue and other structures which can close off the upper airway passage.

A need exists for an apparatus to treat obstructive sleep apnea without major surgical intervention. A further need exists for an apparatus to reduce a volume of a selected site in an interior of the tongue. Still a further need exists for an apparatus to reduce a volume of a selected site in an interior of the tongue without damaging a main branch of the hypoglossal nerve.

SUMMARY OF THE INVENTION

Accordingly, an object of the invention is to provide an apparatus to reduce a volume of a selected site in an interior of the tongue.

Another object of the invention is to provide an apparatus to reduce a volume of a selected site in an interior of the tongue including an energy delivery device and an energy delivery advancement device, wherein the energy delivery advancement member advances the energy delivery device an advancement distance in the interior of the tongue sufficient for an energy delivery device to deliver energy to the selected tissue site and reduce a volume of the selected site without damaging a main branch of the hypoglossal nerve.

Yet another object of the invention is to provide an apparatus to reduce a volume of a selected site in an interior of the tongue including an energy delivery device and an energy delivery device advancement member, wherein the energy delivery device advancement member advances the energy delivery device to a placement position in an interior of the tongue so that at the placement position an energy delivery device surface can deliver sufficient energy to reduce a volume of the selected site without damaging a main branch of the hypoglossal nerve.

A further object of the invention is to provide an apparatus to reduce a volume of a selected site in an interior of the tongue with an energy delivery device, an energy delivery surface and an energy delivery device advancement length extending from an exterior of a handpiece to the interior of the tongue, wherein the advancement length is sufficient to position the energy delivery device surface at the selected site and deliver sufficient energy to reduce a volume of the selected tissue site without damaging a main branch of the hypoglossal nerve.

Still a further object of the invention is to provide an apparatus to reduce a volume of a selected site in an interior of the tongue that includes an energy delivery device with a geometric shape configured to reduce a volume of the selected site without damaging a main branch of the hypoglossal nerve.

These and other objects of the invention are achieved in an apparatus that reduces a volume of a selected site in an interior of the tongue. The apparatus includes a handpiece and an energy delivery device at least partially positioned in the interior of the introducer. The energy delivery device includes an energy delivery surface and is advanceable from the interior of the handpiece into the interior of the tongue. An energy delivery device advancement member is coupled to the energy delivery device and configured to advance the energy delivery device an advancement distance in the interior of the tongue. The advancement distance is sufficient for the energy delivery surface to deliver energy to the selected tissue site and reduce a volume of the selected site without damaging a main branch of the hypoglossal nerve and/or a surface of the tongue. A cable is coupled to the energy delivery device.

In another embodiment, the energy delivery device advancement member is configured to advance at least a portion of the energy delivery device to a placement position in the interior of the tongue. At the placement position the energy delivery surface delivers sufficient energy to reduce a volume of the selected site without damaging a main branch of the hypoglossal nerve.

In a further embodiment, the energy delivery device has an energy delivery device advancement length that extends from an exterior of the introducer to the interior of the tongue. The advancement length is sufficient to position the energy delivery surface at the selected site and deliver sufficient energy to reduce a volume of the selected tissue site without damaging a main branch of the hypoglossal nerve.

The energy delivery device may be an RF electrode coupled to an RF energy source. A temperature control device can be included that is at least partially positioned in the interior of the introducer and configured to control a tongue surface temperature. A flow rate control device may be coupled to the temperature control device to control a fluid flow rate.

An insulator may be at least partially positioned around an exterior of the electrode and defines the energy delivery surface. Sensors can be positioned at various locations including, at a distal end of the insulator, at the distal end of the energy deliver device and on an exterior surface of the introducer.

In one embodiment, a first sensor is positioned at the distal end of the energy delivery device and a second sensor is positioned at the distal end of the insulator.

A feedback control device can be coupled to the energy delivery device, the sensors and an energy source. Additionally, an infusion medium source may be coupled to the energy delivery device.

BRIEF DESCRIPTION OF THE FIGURES

FIG. 4A–4C are perspective views of a needle energy delivery device associated with the debulking apparatus illustrated in FIGS. 1A–1C.

FIG. 5 is a perspective view of a flexible needle energy delivery device utilized with the methods of the present invention.

DETAILED DESCRIPTION

Figure 1A:
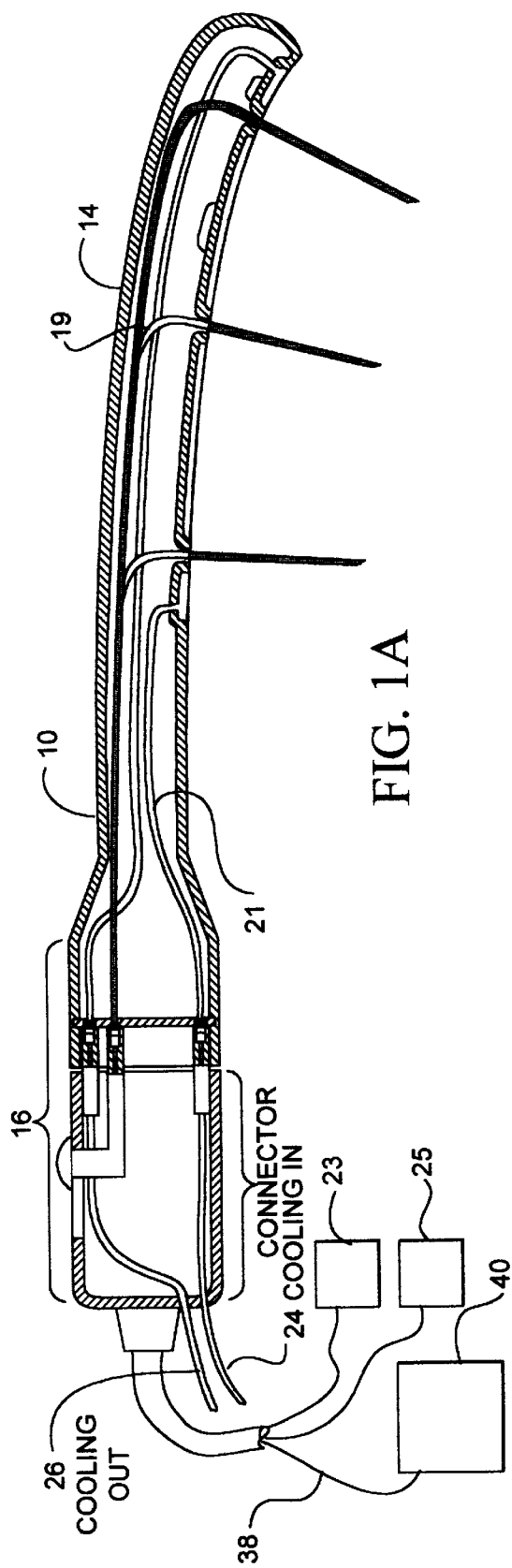
FIGS. 1A–1C are cross-sectional views of an debulking apparatus used with the present invention.

Referring to FIGS. 1A–1C and 2, an ablation apparatus 10, creating controlled ablation and a reduction of a volume of a selected tissue site of an anatomical structure. For purposes of this disclosure the anatomical structure will be referred to as the tongue. It will be appreciated that the apparatus of the present invention is equally useful with the lingual tonsils, soft palate, turbinates, uvula and the like as illustrated. For purposes of this disclosure, an ablation procedure shall be meant to include thermal damage, tissue shrinkage, tissue scarring, remodeling debulking and causing ablation. Ablation apparatus 10 can be positioned to deploy one or more energy delivery devices 12. Each energy delivery device 12 may be a needle energy delivery device and each is introduced into an interior of the tongue through a surface of the tongue. Ablation apparatus 10 may include traumatic intubation with or without visualization, provide for the delivery of oxygen or anesthetics, and can be capable of suctioning blood or other secretions. It will be appreciated that ablation apparatus 10 is used to treat a variety of different obstructions in the body where passage of gas is restricted. One application is the treatment of sleep apnea using energy delivery devices 12 to ablate at selected portions of the tongue by the use of a variety of different energy sources including but not limited to resistive heating, RF, microwave, ultrasound, coherent light, incoherent light, thermal transfer, resistive heating, chemical ablation, cryogenic fluid, electrolytic solutions, and the like. The preferred energy source is an RF source. In one embodiment, ablation apparatus 10 is used to ablate an interior region of the tongue, causing it to become debulked, shrunk, remodeled, or to induce tissue scarring in order to increase the cross-sectional area of the airway passage. A disinfectant medium introduction member introduces a disinfectant medium in the oral cavity in order to reduce infection of the ablated body member.

Prior to ablating the tongue, a presurgical evaluation may be performed including a physical examination, fiber optic pharyngoscopy, cephalometric analysis and polygraphic monitoring. The physical examination emphasizes the evaluation of the head and neck. It also includes a close examination of the nasal cavity to identify obstructing deformities of the septum and turbinate; oropharyngeal obstruction from a long, redundant soft palate or hypertrophic tonsils; and hypopharyngeal obstruction from a prominent base of the tongue.

Ablation apparatus 10 includes an introducer 14, an optional handle 16 and one or more energy delivery devices 12 extending from different ports 18 formed along a longitudinal surface of introducer 14. Introducer 14 can be a handpiece. An energy delivery advancement device 20 may be provided. Energy delivery advancement device 20 can include guide tracks or tubes 19 positioned in the interior of introducer 14. Energy delivery devices 12 may be positioned in guide tracks 19 and advanced from the guide tracks 19 into the interior of the tongue. Cabling is coupled to energy delivery devices 12. Introducer 14 and handle 16 may be one device.

Controlled volumetric reduction of the tongue, under feedback control, is used to achieve an effective opening in the airway passage. A variety of different pain killing medicaments, including but not limited to Xylocaine, may be used. A digital ultrasonic measurement system can be used. The ultrasound measurement quantifies biological shape changes, provides ultrasonic transmission and reception, uses piezoelectric transducers (crystals) and provides time of flight data.

A disinfectant medium introduction member 21 may be included and introduced into the oral cavity. Disinfectant medium introduction member 21 can be introduced before, after or during the introduction of ablation apparatus 10 into the oral cavity. Additionally, disinfectant medium introduction member 21 can be removed at the same time or at a different time that ablation apparatus 10 is removed from the oral cavity. Disinfectant medium introduction member 21 can be included in ablation apparatus 10, in an interior of introducer 14 or at an exterior of introducer 14, and may be an introducer with a lumen configured to introduce a disinfectant agent from a disinfectant agent source 23 into all or a selected portion of the oral cavity. Disinfectant medium introduction member 21 can be capable of movement within the oral cavity in order to provide for disinfection of all or only a portion of the oral cavity. For purposes of this disclosure, the oral cavity is that body internal environment where infectious germs may be introduced into the ablated tongue, soft tissue structure, and the like. Disinfectant medium introduction member 21 may be slidably positioned in introducer 14 or at its exterior. Alternatively, disinfectant medium introduction member 21 can be an optical fiber coupled to a light energy source, including but not limited to a UV source 25. The optical fiber can also be slidably be positioned in the oral cavity. The optical fiber is configured to provide for the selective disinfection of all or only a portion of the oral cavity and can have a variety of different distal ends to achieve this purpose.

Suitable disinfectant agents include but are not limited to Peridex, an oral rinse containing 0.12% chlorhexidine glucinate (1, 1'-hexanethylenebis[5-(p-chlorophenyl)biganide} di-D-gluconate in a base containing water, 11.6% alcohol, glycerin, PEG 40 sorbitan arisoterate, flavor, dosium saccharin, and FD&C Blue No. 1.

It will be appreciated that a variety of different disinfectants can be employed, including other wavelengths, and various chemical compositions and mixtures.

Energy delivery devices 12 are at least partially positioned in an interior of introducer 14. Each energy delivery device 12 is advanced and retracted through a port 18. Energy delivery device advancement and retraction device advances energy delivery devices 12 out of introducer 14, into an interior of the tongue and can also provide a retraction of energy delivery devices 12 from the interior of the tongue. Energy delivery devices 12 pierce an exterior surface of the tongue and are directed to an interior region of the tongue. Sufficient energy is delivered by energy delivery devices 12 to the interior of the tongue to cause the tongue to become sufficiently ablated. Energy delivery devices 12 can be hollow to receive a variety of different infusion mediums, including but not limited to saline. Energy delivery devices 12 may be limited in the distance that they can be advanced into the tongue. A means for limiting the travel of energy delivery devices 12 may be provided. The limiting stop may be adjustable to provide variability in the amount energy delivery devices 12 travel. This may be achieved with an insulation sleeve that is in a surrounding relationship to an exterior of energy delivery device 12. See also FIG. 3.

Energy delivery devices 12 can include a central lumen for receiving a variety of fluids that can be introduced into the interior of the tongue, as well as a plurality of fluid delivery ports. In one embodiment, the disinfectant agent is introduced through energy delivery devices 12 into the interior of the tongue. Another suitable fluid is an electrolytic solution to enhance the delivery of energy fro energy delivery device 12. Energy delivery can be direct from energy delivery device to tissue, indirect from energy delivery device 12 to electrolytic solution to tissue, or a combination of the two to deliver the thermal energy to the tissue. This can be used in order to provide an enhanced energy delivery device beyond a stand alone energy delivery device. Another suitable fluid is a temperature control fluid which controls a tongue surface temperature in the range of 10–45 degrees C.

Introducer 14 includes an introducer tissue interface surface 22, a temperature control medium inlet conduit 24 and a temperature control medium outlet conduit 26 extending through an interior of introducer 14. Ports 18 are formed in the exterior of introducer 14, and are preferably formed on introducer tissue interface surface 22. Ports 18 are isolated from a temperature control medium flowing in inlet and outlet conduits 24 and 26. Temperature control medium inlet and outlet conduits 24 and 26 are configured to provide a temperature controlled section of introducer tissue interface surface 22 with a radius of at least 1 to 2 cm². In one embodiment, the temperature controlled section of introducer tissue interface surface 22 is at least equal to the cross-sectional diameter of the underlying zone of the ablation area. In another embodiment, the temperature controlled section of introducer tissue interface surface 22 only provides temperature control to an area associated with each deployed energy delivery device 12.

The sizes of the temperature control section are sufficient to minimize swelling of the tongue following delivery of energy. The reduction of swelling can be 50% or greater, 75% or greater, and 90% and greater. The amount of temperature control provided is sufficient to enable the patient to return home shortly after the ablation procedure is performed. This reduces the risk of choking on the tongue due to swelling. It has been found that by providing a sufficient level of temperature control over a relatively large area, the amount of ablation in an interior region of the tongue is enhanced without incurring thermal damage at the surface of the tongue. This preserves the senses of taste and touch. By providing a large enough temperature controlled section of introducer tissue interface surface 22, an edematous response is minimized.

An energy delivery surface 30 of energy delivery device 12 can be adjusted by inclusion of an adjustable or non-adjustable insulation sleeve 32 (FIGS. 4A–4C and 5). Insulation sleeve 32 can be advanced and retracted along the exterior surface of energy delivery device 12 in order to increase or decrease the length of the energy delivery surface 30. Insulation sleeve 32 can be made of a variety of materials including but not limited to nylon, polyimides, other thermoplastics and the like. The size of energy delivery surface 30 can be varied by other methods including but not limited to creating a segmented energy delivery device 12. Additionally, a plurality of energy delivery devices 12 can be multiplexed and individually activated, and the like.

Referring specifically to FIGS. 4A–4C, energy delivery device 12 has an advancement length 33 that extends from an exterior surface of introducer 14 and is directed into the interior of the tongue. Advancement length 33 is sufficient to position energy delivery surface 30 at a selected tissue site in the interior of the tongue. Energy delivery surface 30 is of sufficient length so that energy is delivered to the selected tissue site and create a desired level of ablation at the selected tissue site without causing damage to the main branches of the hypoglossal nerve. For purposes of this disclosure, the main branches of the hypoglossal nerve are those branches which if damaged create an impairment, either partial or full, of speech or swallowing capabilities. Energy delivery surface 30 is not always at the distal end of energy delivery device 12. Insulation 32 can also be positioned at the distal end of energy delivery device 12. In this embodiment, energy delivery surface 30 does not extend to the distal end of energy delivery device 12. However, energy delivery surface 30 still delivers sufficient energy to create a desired level of ablation in the interior of the tongue at the selected tissue site without damaging the main branches of the hypoglossal nerve and/or damage to the surface of the tongue to permanently alter the sense of taste. Additionally, only one side or a portion of a side of energy delivery device 12 can be insulated. This permits energy delivery device 12 to be positioned throughout the tongue, including adjacent to a main branch of the hypoglossal nerve. Where energy delivery device 12 is adjacent to the main branches of the hypoglossal nerve, energy delivery device 12 is insulated.

In one embodiment, advancement length 33 is 1.2 to 1.5 cm, and the length of energy delivery surface 30 is 5 to 10 mm, more preferably about 8 mm.

In another embodiment, advancement length 33 is insufficient to reach the main branches of the hypoglossal nerve when introduced through any of the tongue surfaces, particularly the dorsum of the tongue.

Energy delivery device advancement device 20 is configured to advance at least a portion of each energy delivery device 12 to a placement position in the interior of the tongue. Energy delivery device advancement device 20 can also be configured to retract each energy delivery device 12. At the placement position, energy delivery device 12 delivers sufficient energy to reduce a volume of the selected site without damaging a hypoglossal nerve and/or a surface of the tongue. In one embodiment, energy delivery device advancement and retraction device 20, with or without guide tracks 19, directs the delivery of an energy delivery device 12 from introducer 14 into the interior of the tongue at an angle of 60 to 90 degrees relative to a longitudinal axis of introducer 14, and preferably about 70 degrees.

Each energy delivery device 12 has a geometric shape, including but not limited to a curved configuration that includes one or more insulated surfaces, either partially insulated on one side, at a proximal end, at a distal end, and the like and is configured to reduce the volume of the selected tissue site without damaging a hypoglossal nerve. In one embodiment, energy delivery device 12 is introduced through any tongue surface and is configured so that a section of energy delivery device 12 with insulation sleeve 32 may be positioned close to the main branches of the hypoglossal nerve. As previously noted, insulation sleeve 32 can be positioned at different sites of energy delivery device 12.

Referring again to FIGS. 1A–1C, handle 16 is preferably made of thermal and electrical insulating material. Energy delivery devices 12 are made of a conductive material such as stainless steel. Additionally, energy delivery devices 12 can be made of a shaped memory metal, such as nickel titanium. In one embodiment, only a distal end of energy delivery device 12 is made of the shaped memory metal in order to effect a desired deflection. When introduced into the oral cavity, introducer 14 can be advanced until a patient's gag response is initiated. Introducer 14 is then retracted back to prevent patient's gagging. The distal end of energy delivery device 12 can be semi-curved. The distal end can also have a geometry to conform to an exterior of the tongue.

In one embodiment of the invention introducer 14 is a handpiece. For purposes of this embodiment, introducer 14 shall be referred to as handpiece 14. In this embodiment, a separate handle 16 is not necessary. Ablation apparatus 10 is used to treat an interior region of the tongue. Handpiece 14 has a distal end sized to be positioned within an oral cavity. Energy delivery device 12 is at least partially positioned within an interior of handpiece 14. Energy delivery device 12 includes an energy delivery surface 30. Energy delivery device advancement member 20 is coupled to energy delivery device 12 and calibrated to advance energy delivery device 12 from handpiece 14, including but not limited to a distal end of handpiece 14, into the interior of the tongue when handpiece 14 is positioned adjacent to a surface of the tongue. Energy delivery device 12 is advanced an advancement distance 33 from handpiece 14 of sufficient length to treat the interior region of the tongue with energy without damaging the main branches of the hypoglossal nerve or the surface of the tongue.

Introducer 14 can be malleable in order to conform to the surface of the tongue when a selected ablation target site is selected. A soft metal member may be enclosed or encapsulated within a flexible outer housing to form malleable introducer 14.

In another embodiment (see FIG. 1B), a separate handle 16, a distal end 14' of introducer 14 is conformable or deflectable. This can be achieved mechanically or with the use of memory metals. A steering wire, or other mechanical structure, can be attached to either the exterior or interior of distal end 14'. In one embodiment, a deflection knob located on handle 16 is activated by the physician causing a steering wire to tighten (not shown). This imparts a retraction of distal end 14', resulting in its deflection. It will be appreciated that other mechanical devices can be used in place of the steering wire. The deflection may be desirable for tissue sites with difficult access.

Figure 1C:
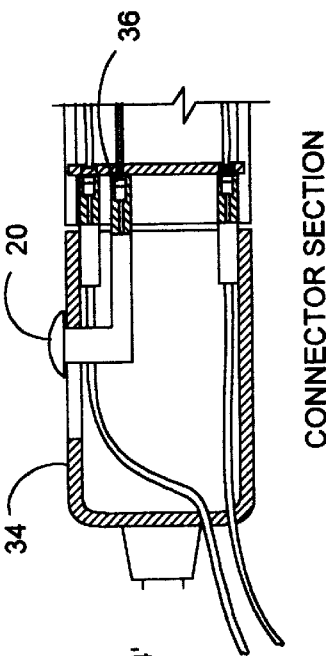
Figure 1B:
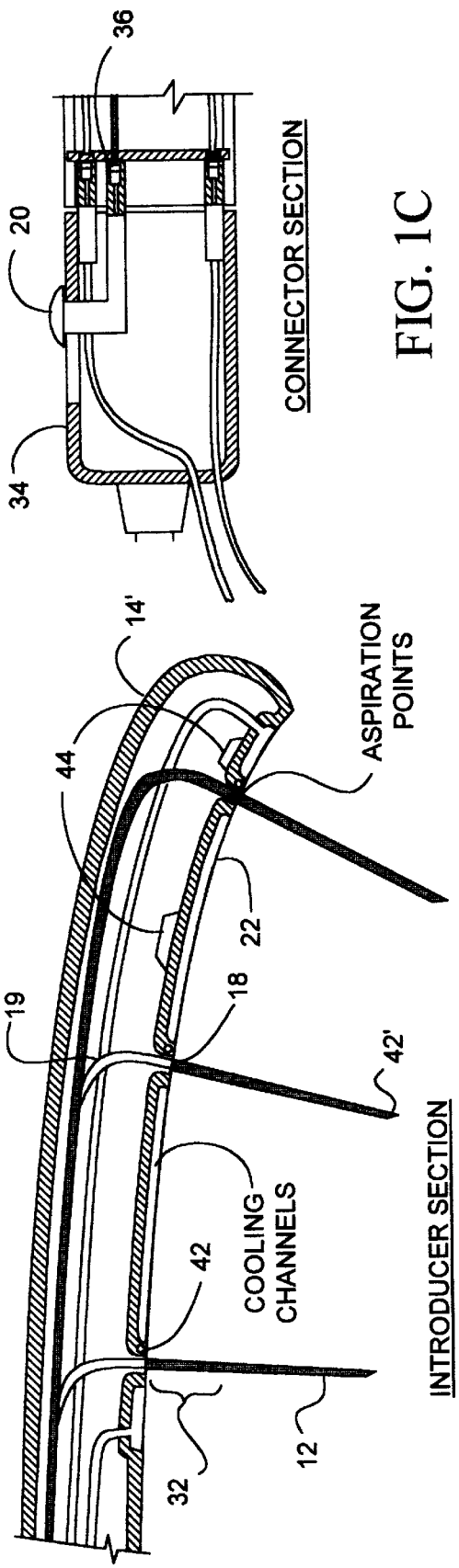
Figure 2:
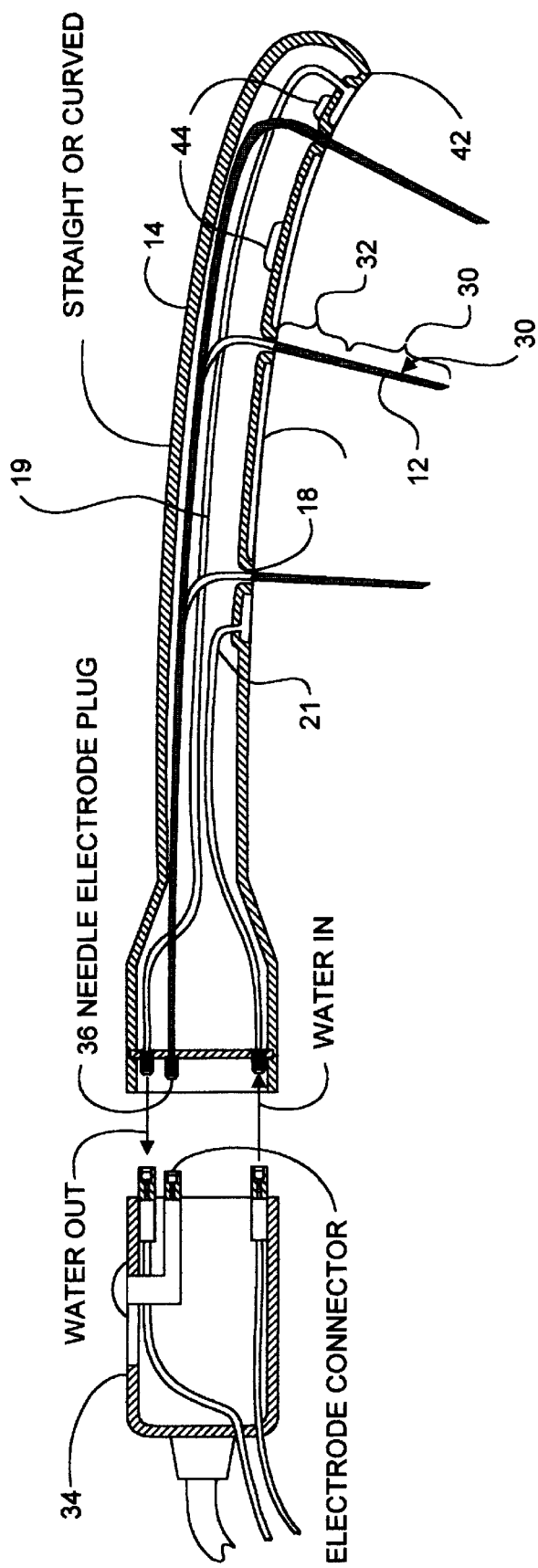
FIG. 2 is cross-sectional view illustrating the introducer and connector of the debulking apparatus shown in FIGS. 1A–1C.
Figure 3:
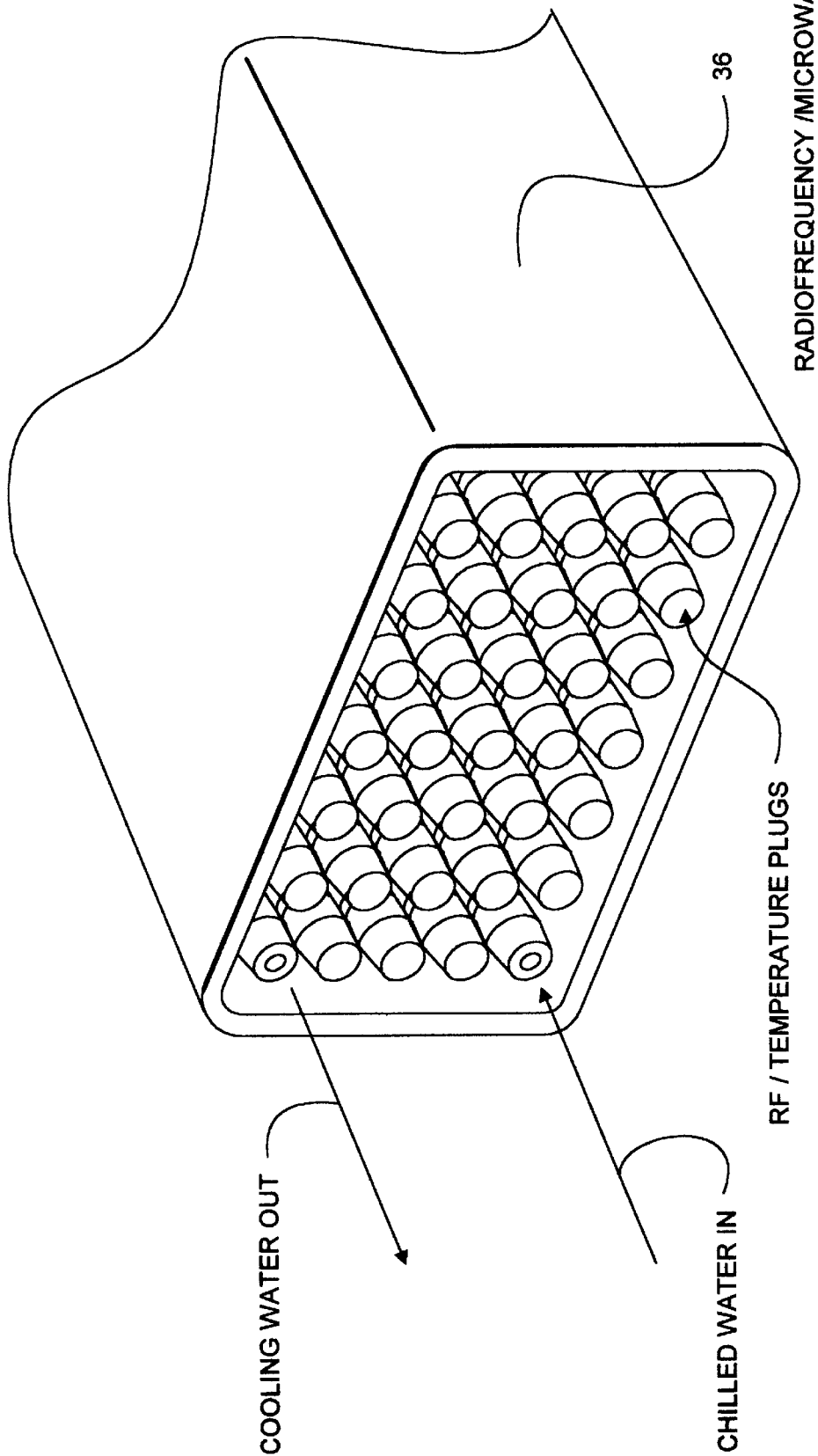
FIG. 3 is a perspective view of the connector illustrated in FIGS. 1A–1C.

In FIGS. 1C and 2, handle 16 can include a connector 34 coupled to retraction and advancement device 20. Connector 34 provides a coupling of energy delivery devices 12 to power, feedback control, temperature and/or imaging systems. A temperature control block 36 can be included (FIG. 3).

In one embodiment, the physician moves retraction and advancement device 20 in a direction toward a distal end of connector 34. Energy delivery devices 12 can be spring loaded. When energy delivery device advancement device 20 is moved back, springs cause selected energy delivery devices 12 to advance out of introducer 14.

One or more cables 38 couple energy delivery devices 12 to an energy source 40. A variety of energy sources 40 can be used with the present invention to transfer energy to the interior of a body structure, including but not limited to RF, microwave, ultrasound, coherent light, incoherent light, resistive hearing, chemical ablation, cryogenic fluids, electrolytic solutions and thermal transfer. Preferably, energy source 40 is a RF generator. When a RF energy source is used, the physician can activate RF energy source 40 by the use of a foot switch (not shown) coupled to RF energy source 40. Energy delivery device 12 may be a needle electrode. One or more sensors 42 may be used to measure temperatures. For purposes of this specification, sensors which are not introduced into an interior of a body structure are denoted as 42. Sensors which are introduced into the body structure are denoted as 42'.

One or more sensors 42 and 42' may be positioned on an interior or exterior surface of energy delivery device 12, insulation sleeve 32, or be independently inserted into the interior of the body structure.

Sensors 42 and 42' permit accurate measurement of temperature at a tissue site and if a predetermined maximum temperature is exceeded, the energy power supply/controller will reduce or shut down the power being delivered. By monitoring the temperature and modulating the energy delivered, sensors 42 and 42' prevent non-targeted tissue from being destroyed or ablated.

Sensors 42 and 42' are of conventional design, including but not limited to thermistors, thermocouples, resistive wires, and the like. Suitable sensors 42 include a T type thermocouple with copper constant an, J type, E type, K type, fiber optics, resistive wires, thermocouple IR detectors, and the like. It will be appreciated that sensors 42 need not be thermal sensors.

Sensors 42 can measure the temperature at various points within the interior of the body structure. The data collected may be used to determine the temperature attained and by comparing the rate of rise against time, power level and impedance, the size and extent of lesion may be computed.

If at any time sensors 42 and 42' determine that a desired temperature is exceeded, then an appropriate feedback signal is received at energy source 40 and the amount of energy delivered is regulated.

Ablation apparatus 10 can include visualization capability including but not limited to a viewing scope, ultrasound, an expanded eyepiece, fiber optics, video imaging, and the like.

Additionally, an ultrasound transducer 44 can determine the size and position of the created lesion. In one embodiment, two ultrasound transducers are positioned on opposite sides of introducer 14 to create an image depicting the lesion in the tongue. Each ultrasound transducer 44 is coupled to an ultrasound source (not shown).

Figure 6:
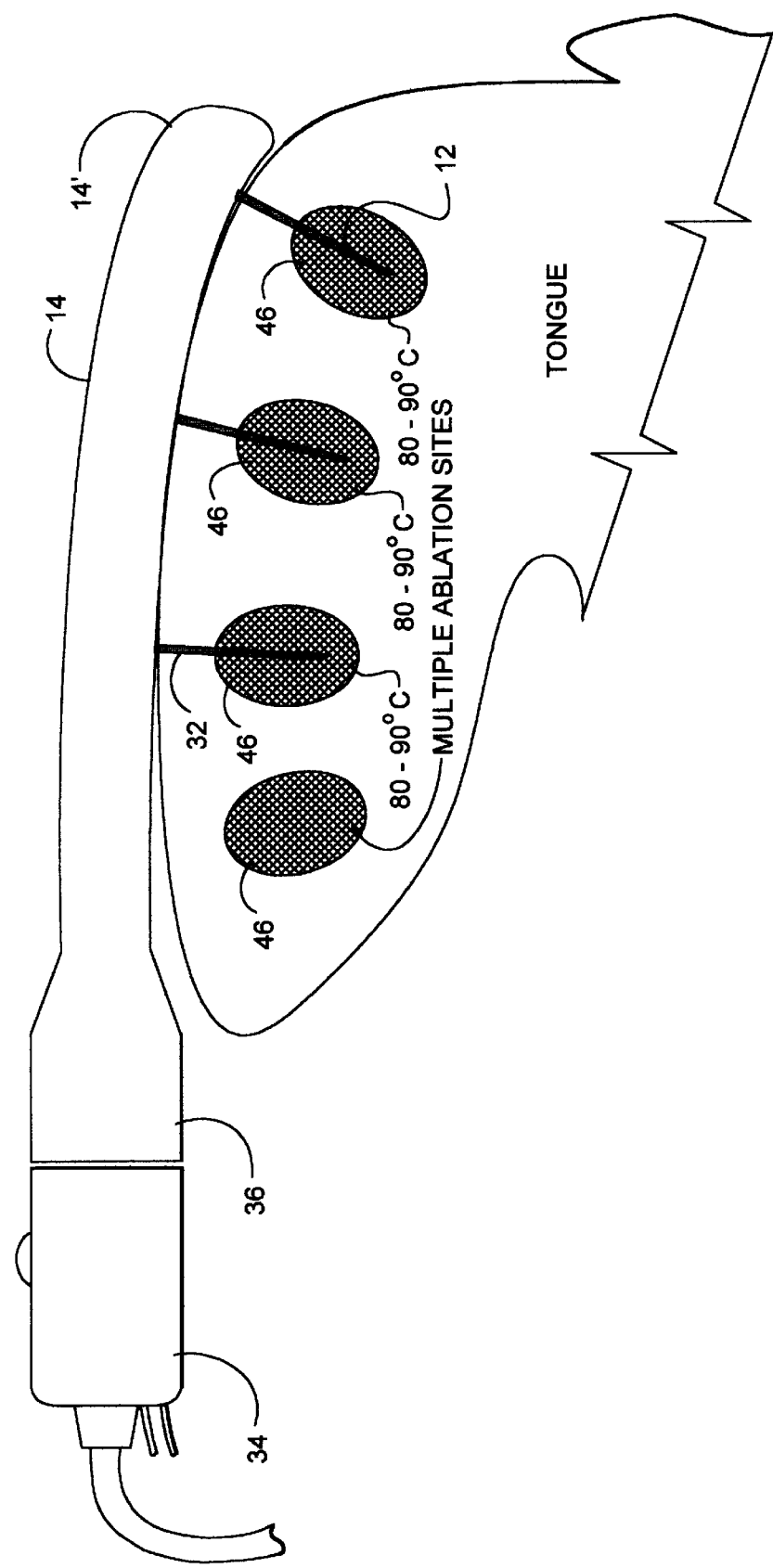
FIG. 6 illustrates the creation of ablation zones with the debulking apparatus shown in FIGS. 1A–1C.
Figure 7:
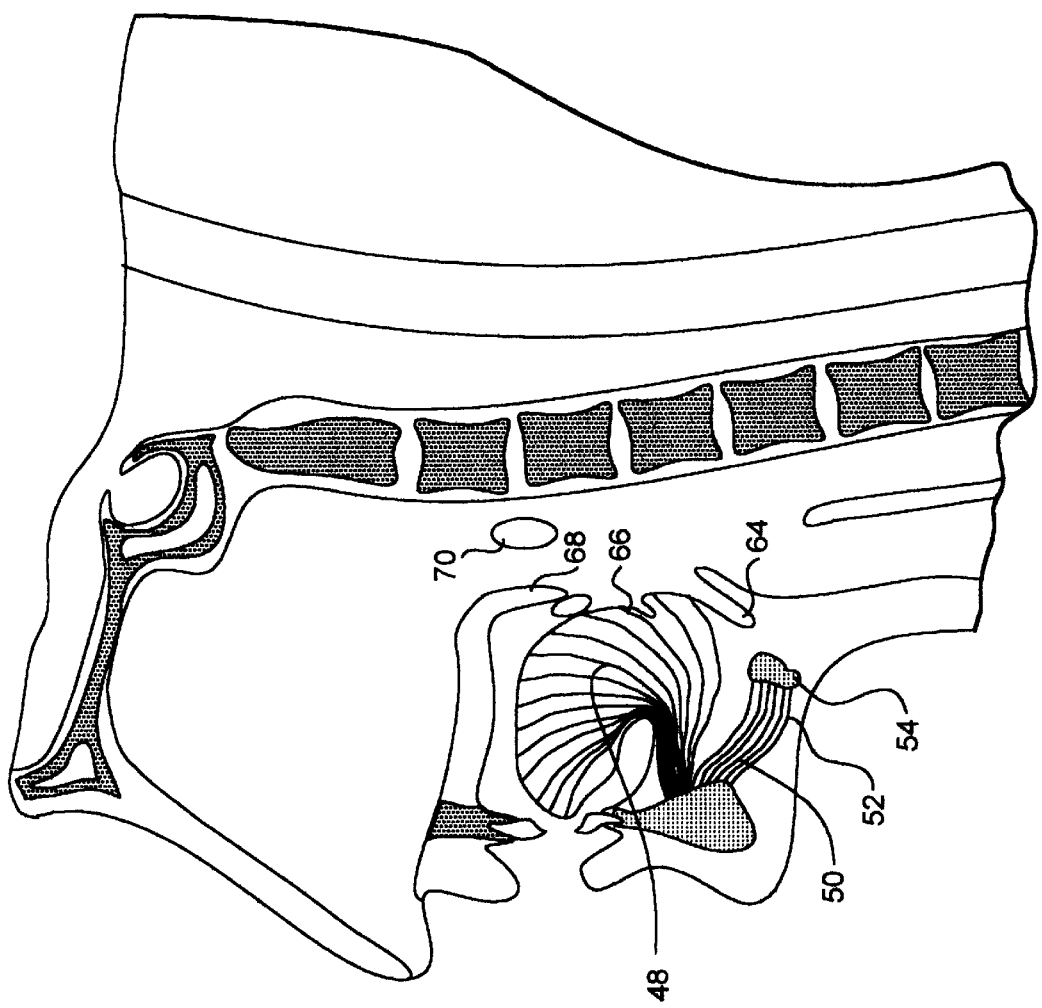
FIG. 7 is a cross-sectional view of the tongue with the mouth closed.
Figure 8:
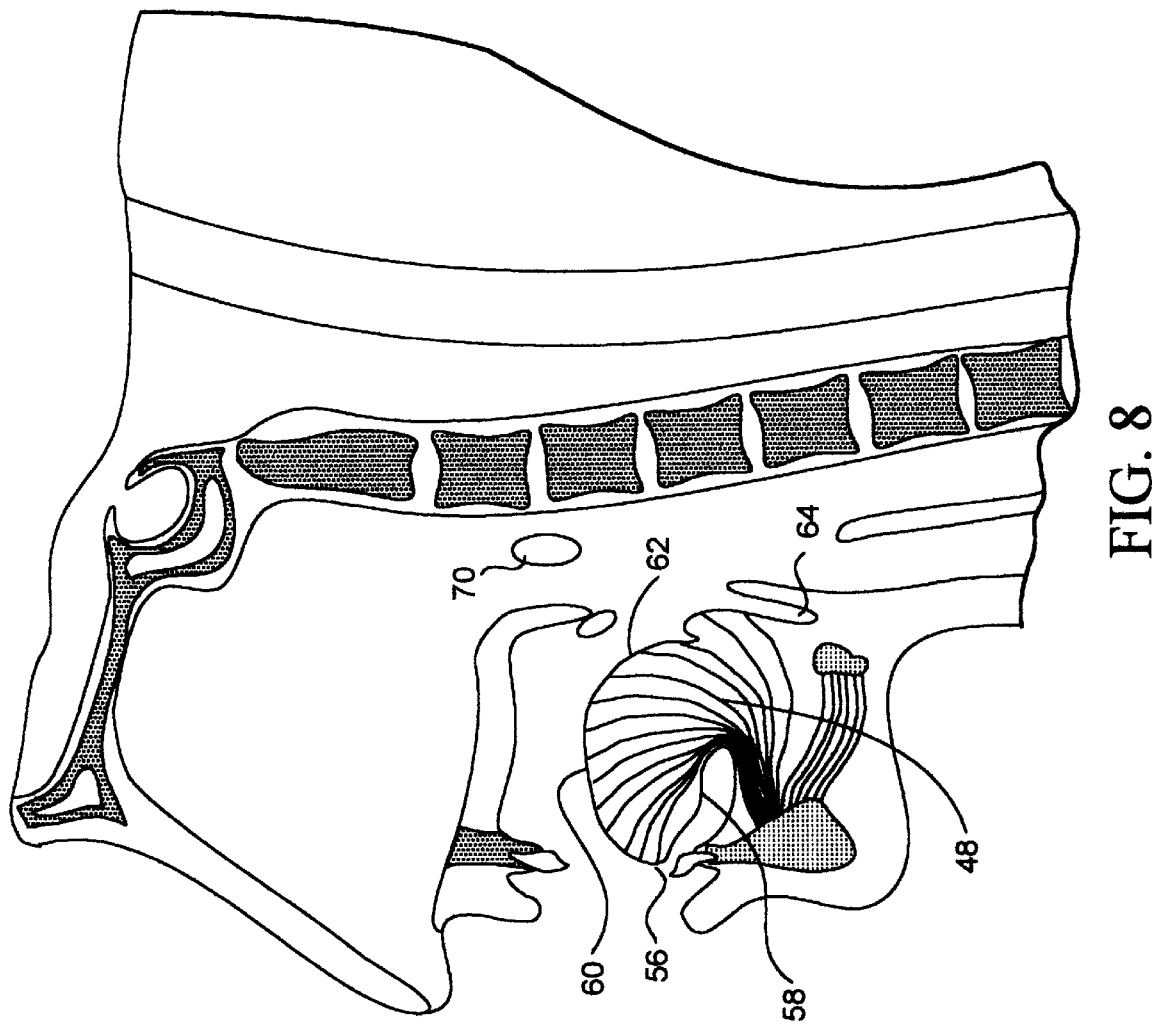
FIG. 8 is a cross-sectional view of the tongue with the mouth open.
Figure 9:
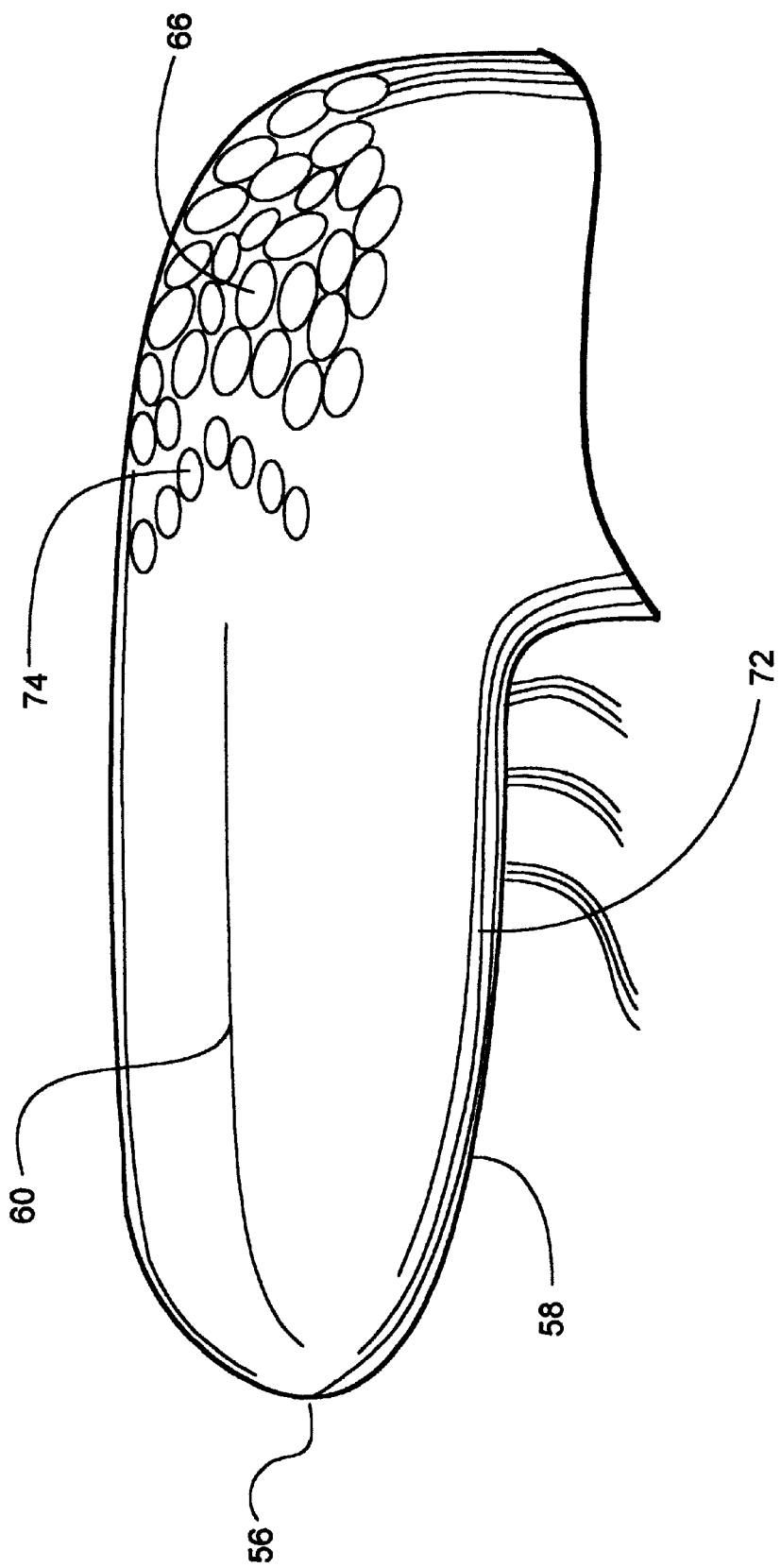
FIG. 9 is a perspective view of the tongue.
Figure 11:
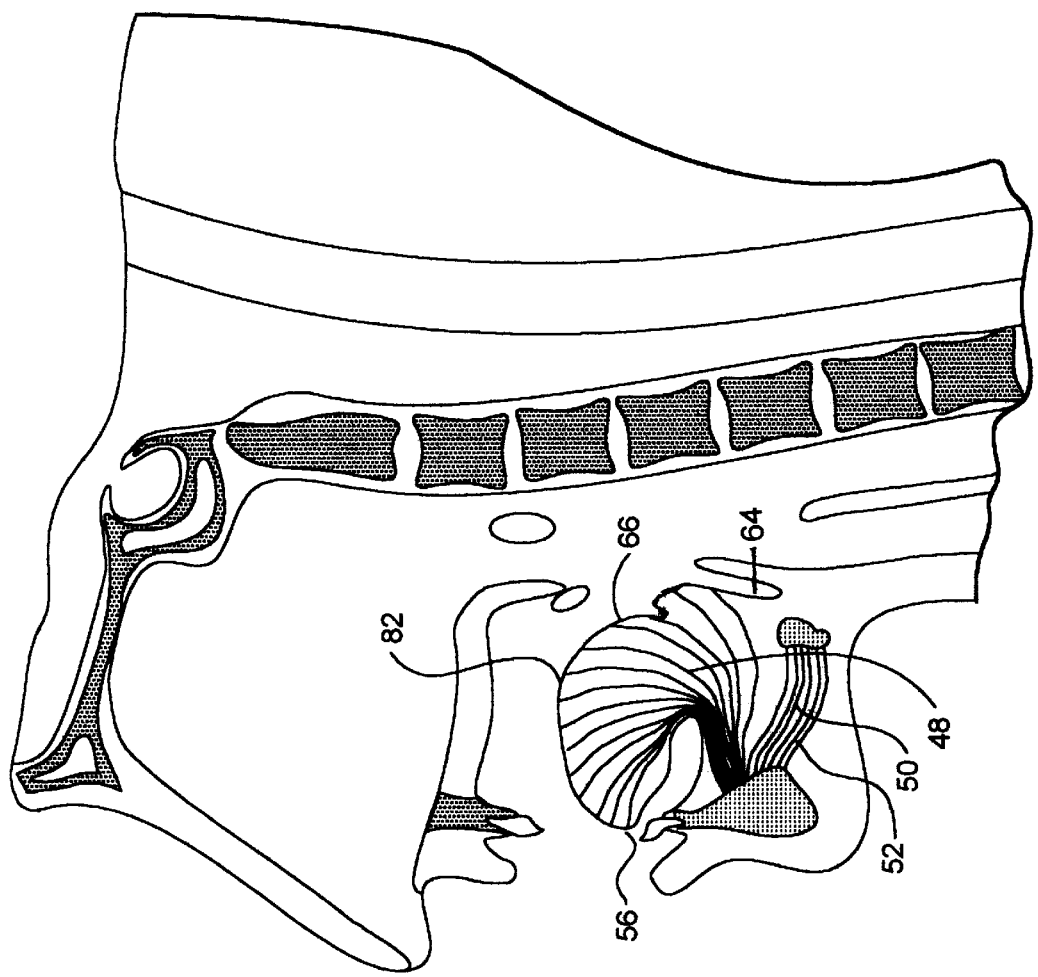
FIG. 11 is a cross-sectional view of the tongue.
Figure 10:
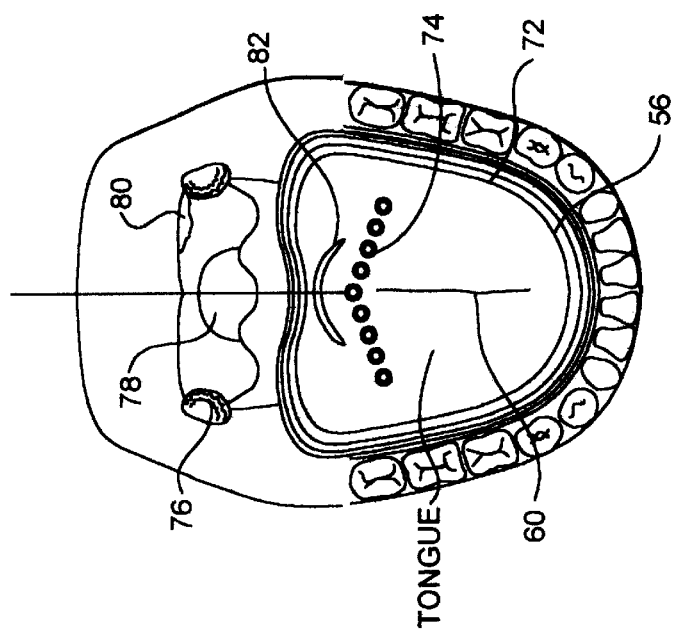
FIG. 10 is a perspective view of the dorsum of the tongue.
Figure 13:
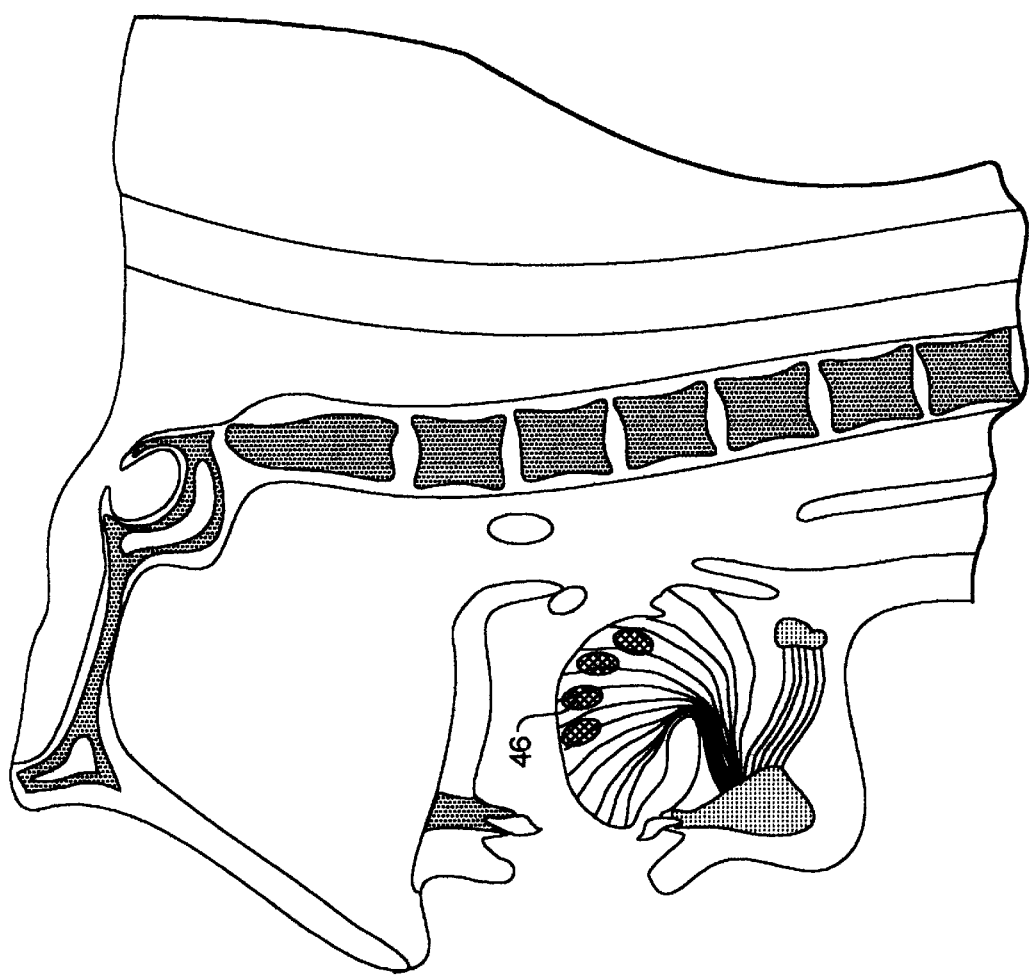
FIG. 13 is a cross-sectional view of the tongue illustrating a plurality of ablation zones.
Figure 12:
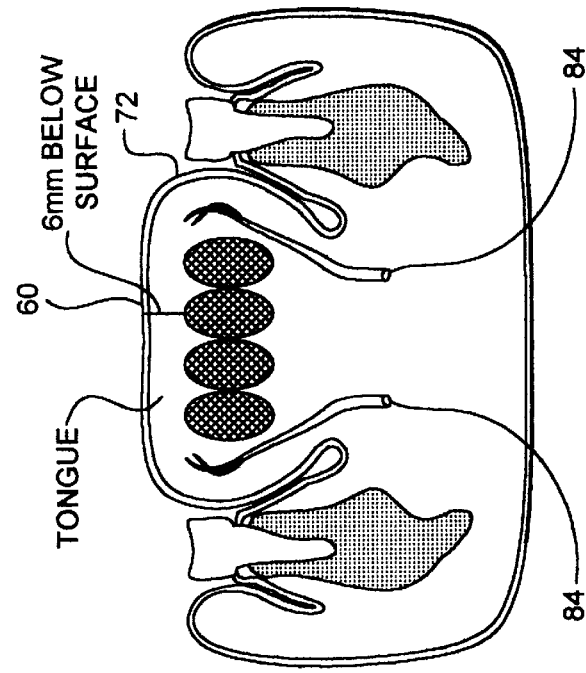
FIG. 12 is a cross-sectional view of the tongue illustrating the location of the main branches of the hypoglossal nerve and the creation of a ablation zone.
Figure 15:
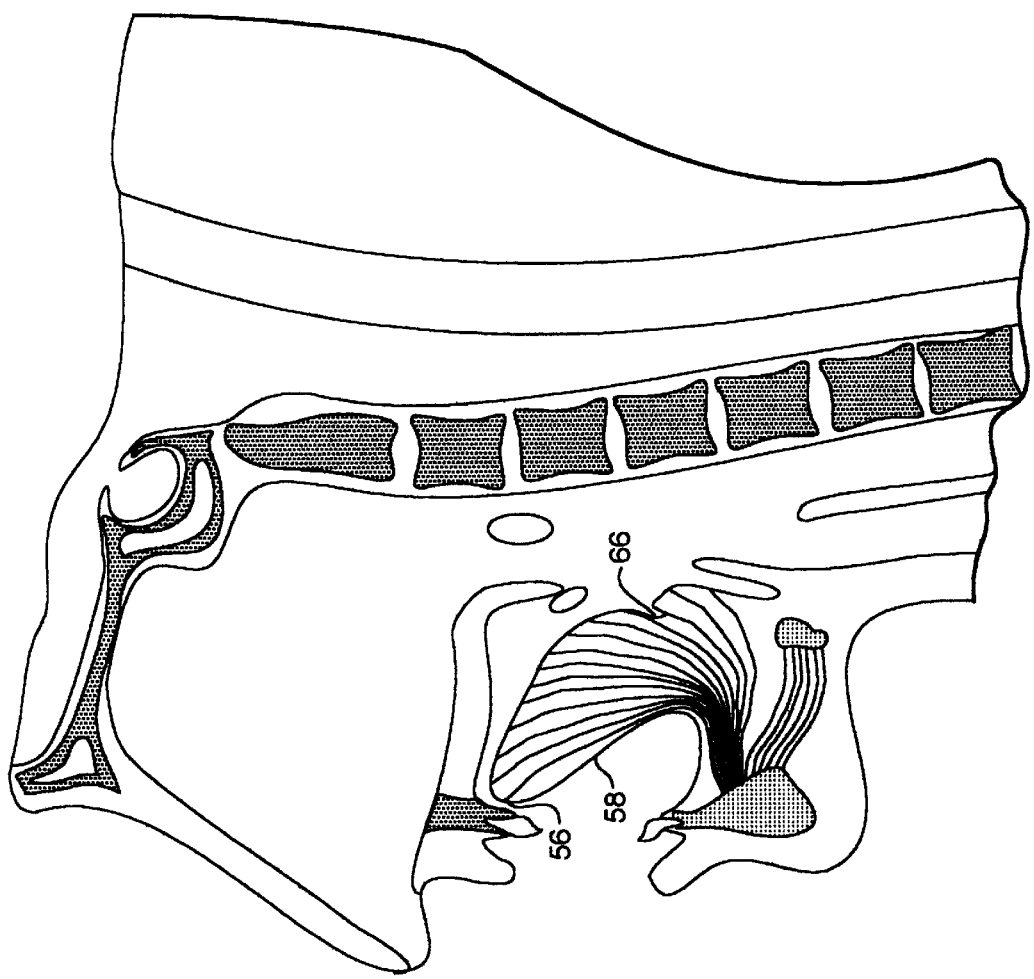
FIG. 15 is a cross-sectional view of the tongue.
Figure 14:
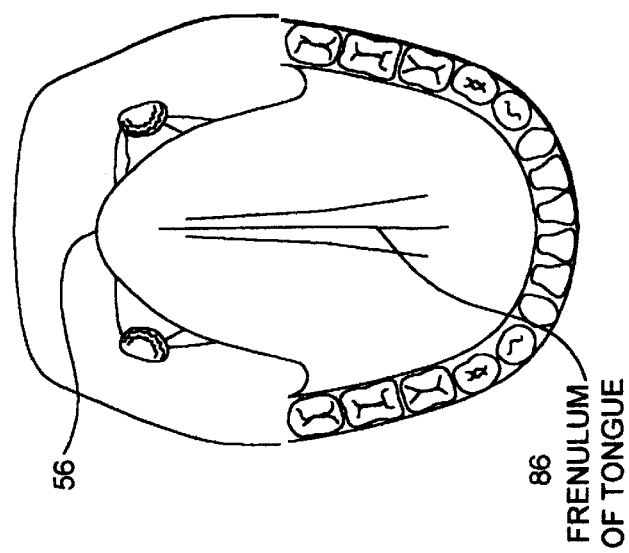
FIG. 14 is a perspective view of the ventral surface of the tongue.

With reference now to FIG. 6 introducer 14 is shown as being introduced into the oral cavity and multiple RF electrodes 12 are advanced into the interior of the tongue creating different ablation zones 46. Ablation apparatus 10 can be operated in either bipolar or monopolar modes with a ground pad). Electrodes 12 are operated in either mode to create ablation zones 46 in the tongue without affecting the main branches of the hypoglossal nerve. A larger airway passage is created. Creation of the ablation zone in the tongue results in a shrinkage of tissue, reshapes the posterior surface of the tongue, and debulks the tongue. The result is an increase in the cross-sectional diameter of the air passageway.

In one embodiment, a single RF electrode 12 is positioned in the tongue to create a first ablation zone 46. Electrodes 12 can then be retracted from the interior of the tongue, introducer 14 moved, and energy delivery device 12 is then advanced from introducer 14 into another interior section of the tongue. A second ablation zone 46 is created. This procedure can be completed any number of times to form different ablation regions in the interior of the tongue. Electrodes 12 are then repositioned in the interior of the tongue any number of times to create a plurality of connecting or non-connecting ablation zones 46 in either bipolar or monopolar mode.

Referring now to FIGS. 7 through 15, various anatomical views of the tongue and other structures are illustrated. The different anatomical structures are as follows: the genioglossus muscle, or body of the tongue is denoted as 48; the geniohyoid muscle is 50; the mylohyoid muscle is 52; the hyoid bone is 54; the tip of the tongue is 56; the ventral surface of the tongue is denoted as 58; the dorsum of the tongue is denoted as 60; the inferior dorsal of the tongue is denoted as 62; the reflex of the vallecula is 64; the lingual follicles are denoted as 66; the uvula is 68; the adenoid area is 70; the lateral border of the tongue is 72; the circumvallate papilla is 74, the palatine tonsil is 76; the pharynx is 78; the redundant pharyngeal tissue is 80; the foramen cecum is 82; the main branches of the hypoglossal nerve are 84, and the lingual frenum of the tongue is 86.

Dorsum 60 is divided into an anterior 2/3 and inferior dorsal 62. The delineation is determined by circumvallate papilla 74 and foramen cecum 82. Inferior dorsal 62 is the dorsal surface inferior to circumvallate papilla 74 and superior reflex of the vallecula 64. Reflex of the vallecula 64 is the deepest portion of the surface of the tongue contiguous with the epiglottis. Lingual follicles 66 comprise the lingual tonsil.

Energy delivery devices 12 can be inserted into an interior of the tongue through dorsum surface 60, inferior dorsal surface 62, ventral surface 58, tip 56 or geniohyoid muscle 50. Additionally, energy delivery devices 12 may be introduced into an interior of lingual follicles 66 and into adenoid area 70. In all instances, the positioning of energy delivery devices 12, as well as the creation of ablation zones 46 is such that the main branches of the hypoglossal nerve 84 are not ablated or damaged. The ability to swallow and speak is not impaired. This creates a larger air way passage and provides a treatment for sleep apnea.

Electrodes may be positioned on the dorsum surface 60 of the tongue. In this embodiment, electrode 12 is an RF electrode. The first RF electrode is positioned 0.5 cm proximal to the circumvallate papilla. The other energy delivery devices are spaced 1.6 cm apart and are 1 cm off a central axis of the tongue. In one embodiment, 465 MHz RF was applied. The temperature at the distal end of energy delivery device 12 was about 100 degrees C. The temperature at the distal end of the insulation sleeve 32 was about 60 degrees C. In another embodiment, the temperature at the distal end of insulation sleeve 32 was 43 degrees C. and above. RF energy can be applied as short duration pulses with low frequency RF. Precise targeting of a desired ablation site is achieved. One or more RF electrodes 12 may be used to create volumetric three-dimensional ablation. A variety of ablation geometries are possible, including but not limited to rectilinear, polyhedral, predetermined shapes, symmetrical and non-symmetrical.

Figure 16:
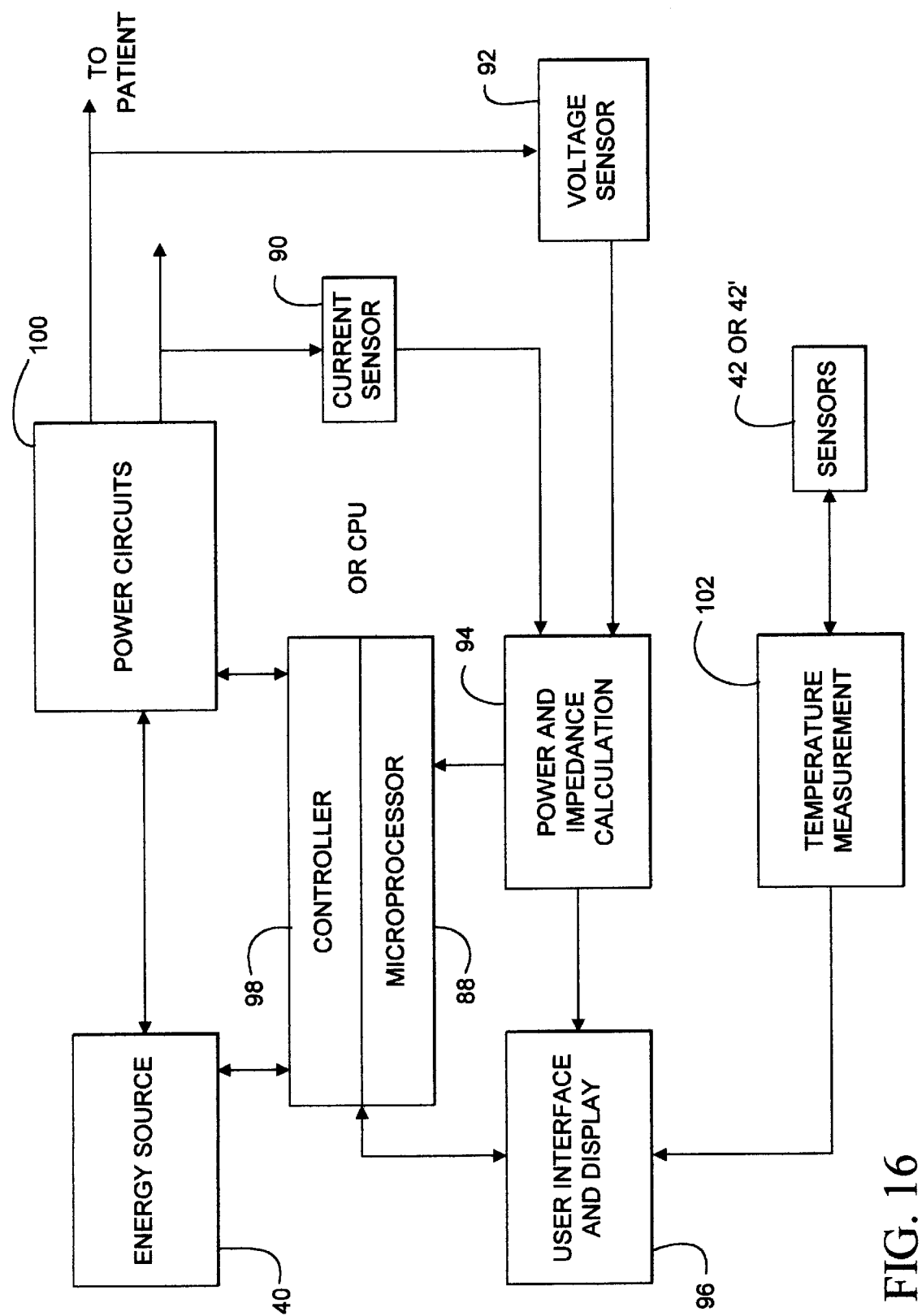
FIG. 16 is a block diagram of a feedback control system useful with the methods of the present invention.

Referring now to FIG. 16 an open or closed loop feedback system couples sensors 42 or 42' to energy source 40. In this embodiment, energy delivery device 12 is one or more RF electrodes. It will be appreciated that other energy delivery devices 12 can also be used with the feedback system.

The temperature of the tissue, or of RF electrode 12 is monitored, and the output power of energy source 40 adjusted accordingly. Additionally, the level of disinfection in the oral cavity can be monitored. The physician can, if desired, override the closed or open loop system. A microprocessor can be included and incorporated in the closed or open loop system to switch power on and off, as well as modulate the power. The closed loop system utilizes a microprocessor 88 to serve as a controller, monitor the temperature, adjust the RF power, analyze at the result, refeed the result, and then modulate the power.

With the use of sensors 42' and the feedback control system a tissue adjacent to RF electrodes 12 can be maintained at a desired temperature for a selected period of time without impeding out. Each RF electrode 12 is connected to resources which generate an independent output. The output maintains a selected energy at RF electrodes 12 for a selected length of time.

Current delivered through RF electrodes 12 is measured by current sensor 90. Voltage is measured by voltage sensor 92. Impedance and power are then calculated at power and impedance calculation device 94. These values can then be displayed at user interface and display 96. Signals representative of power and impedance values are received by a controller 98.

A control signal is generated by controller 98 that is proportional to the difference between an actual measured value, and a desired value. The control signal is used by power circuits 100 to adjust the power output in an appropriate amount in order to maintain the desired power delivered at respective RF electrodes 12.

In a similar manner, temperatures detected at sensors 42' provide feedback for maintaining a selected power. Temperature at sensors 42 are used as safety devices to interrupt the delivery of energy when maximum pre-set temperatures are exceeded. The actual temperatures are measured at temperature measurement device 102, and the temperatures are displayed at user interface and display 96. A control signal is generated by controller 98 that is proportional to the difference between an actual measured temperature and a desired temperature. The control signal is used by power circuits 100 to adjust the power output in an appropriate amount in order to maintain the desired temperature delivered at the respective sensor 42 or 42'. A multiplexer can be included to measure current, voltage and temperature, at the numerous sensors 42, and energy can be delivered to RF electrodes 12 in monopolar or bipolar fashion.

Controller 98 can be a digital or analog controller, or a computer with software. When controller 98 is a computer it can include a CPU coupled through a system bus. On this system can be a keyboard, a disk drive, or other non-volatile memory systems, a display, and other peripherals, as are known in the art. Also coupled to the bus is a program memory and a data memory.

User interface and display 96 includes operator controls and a display. Controller 98 can be coupled to imaging systems, including but not limited to ultrasound, CT scanners, X-ray, MRI, mammographic X-ray and the like. Further, direct visualization and tactile imaging can be utilized.

The output of current sensor 90 and voltage sensor 92 is used by controller 98 to maintain a selected power level at RF electrodes 12. The amount of RF energy delivered controls the amount of power. A profile of power delivered can be incorporated in controller 98 and a preset amount of energy to be delivered may also be profiled.

Circuitry, software and feedback to controller 98 result in process control, and the maintenance of the selected power setting that is independent of changes in voltage or current, and used to change, (i) the selected power setting, (ii) the duty cycle (on-off time), (iii) bipolar or monopolar energy delivery and (iv) fluid delivery, including flow rate and pressure. These process variables are controlled and varied, while maintaining the desired delivery of power independent of changes in voltage or current, based on temperatures monitored at sensors 42 or 42'.

Figure 17:
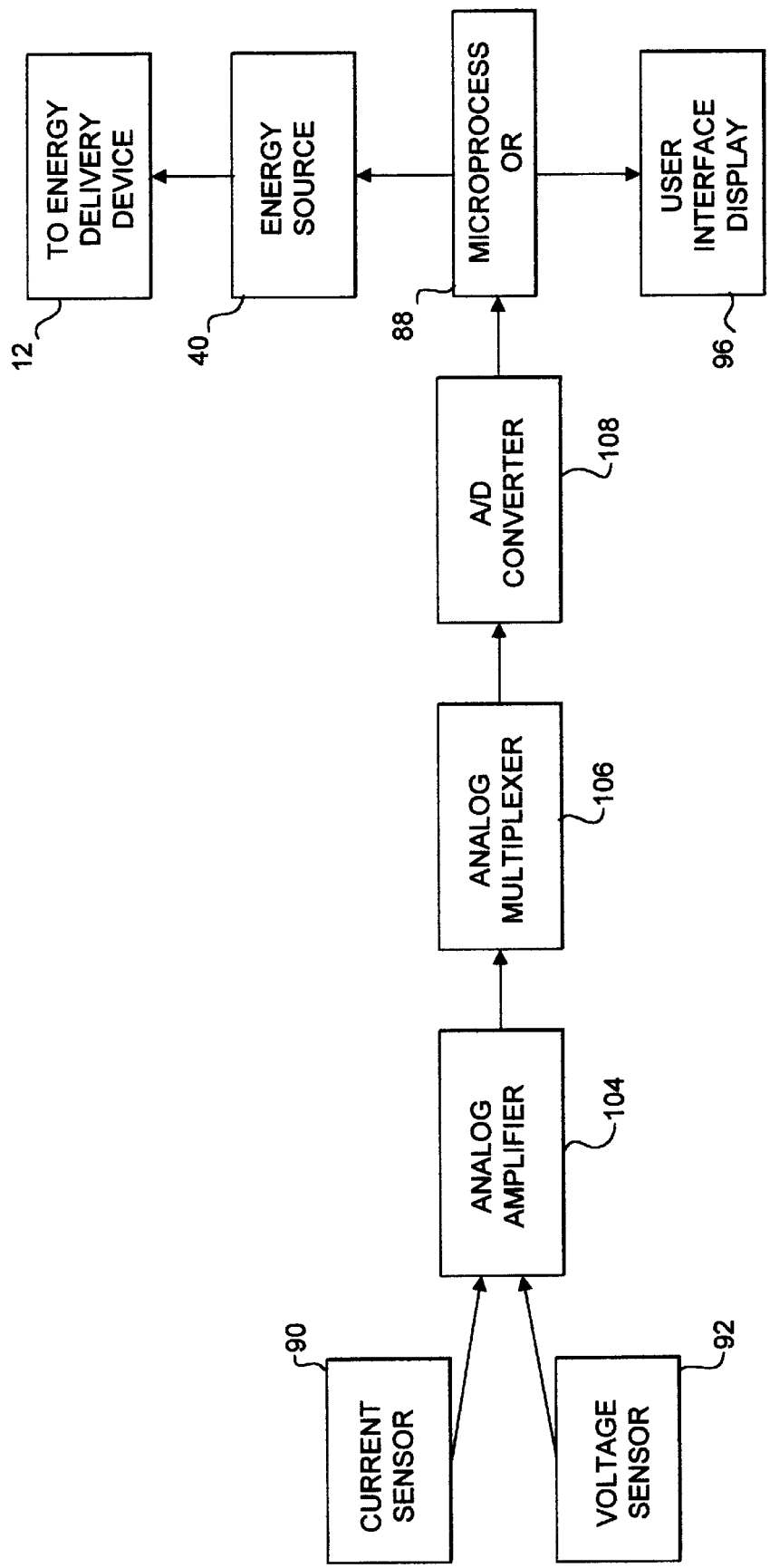
FIG. 17 is a block diagram illustrating an analog amplifier, analog multiplexer and microprocessor used with the feedback control system of FIG. 17.

Referring to FIG. 17, current sensor 90 and voltage sensor 92 are connected to the input of an analog amplifier 104. Analog amplifier 104 can be a conventional differential amplifier circuit for use with sensors 42 or 42'. The output of analog amplifier 104 is sequentially connected by an analog multiplexer 106 to the input of A/D converter 108. The output of analog amplifier 104 is a voltage which represents the respective sensed temperatures. Digitized amplifier output voltages are supplied by A/D converter 108 to microprocessor 88. Microprocessor 88 may be a type 68HCII available from Motorola. However, it will be appreciated that any suitable microprocessor or general purpose digital or analog computer can be used to calculate impedance or temperature.

Microprocessor 88 sequentially receives and stores digital representations of impedance and temperature. Each digital value received by microprocessor 88 corresponds to different temperatures and impedances.

Calculated power and impedance values can be indicated on user interface and display 96. Alternatively, or in addition to the numerical indication of power or impedance, calculated impedance and power values can be compared by microprocessor 88 with power and impedance limits. When the values exceed predetermined power or impedance values, a warning can be given on user interface and display 96, and additionally, the delivery of RF energy can be reduced, modified or interrupted. A control signal from microprocessor 88 can modify the power level supplied by energy source 40.

Figure 18:
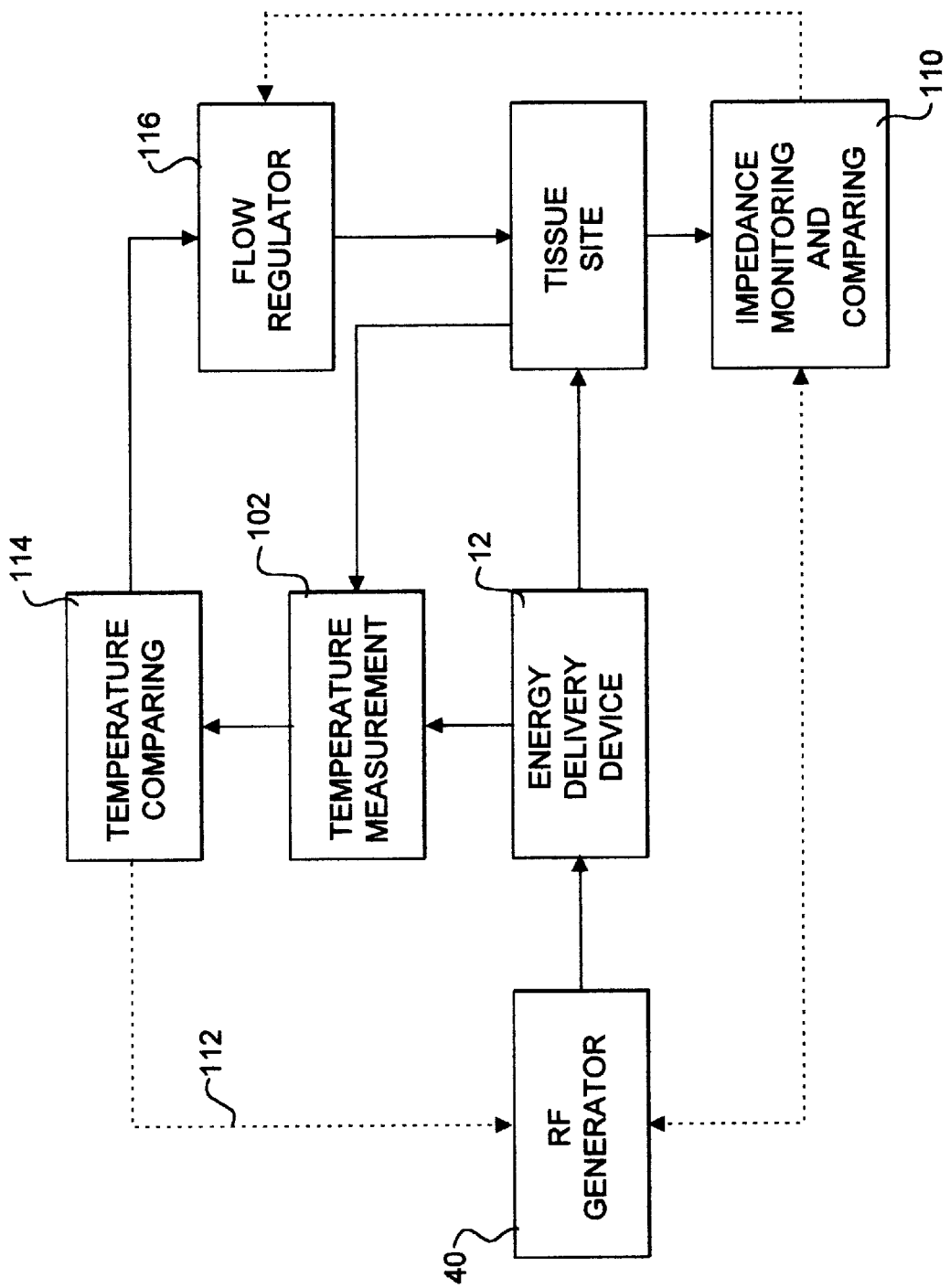
FIG. 18 is a block diagram of a temperature/impedance feedback system that can be used to control cooling medium flow rate through the introducer of FIGS. 1A–1C.

FIG. 18 illustrates a block diagram of a temperature/impedance feedback system that can be used to control temperature control fluid flow rate through introducer 14. Energy is delivered to RF electrodes 12 by energy source 40, and applied to tissue. A monitor 110 ascertains tissue impedance, based on the energy delivered to tissue, and compares the measured impedance value to a sct value. If the measured impedance exceeds the set value a disabling signal 112 is transmitted to energy source 40, ceasing further delivery of energy to electrodes 12. If measured impedance is within acceptable limits, energy continues to be applied to the tissue. During the application of energy sensor 42 and 42' measures the temperature of tissue and/or electrodes 12. A comparator 114 receives a signal representative of the measured temperature and compares this value to a pre-set signal representative of the desired temperature. Comparator 114 sends a signal to a flow regulator 116 representing a need for a higher temperature control fluid flow rate, if the tissue temperature is too high, or to maintain the flow rate if the temperature has not exceeded the desired temperature.

EXAMPLE 1

Ablation apparatus 10 was used to determine two-dimensional shrinkage of a bovine tongue. RF volumetric reduction was achieved using a single needle electrode. Four mature ultrasonic crystals were positioned to form a square. Measurements were taken at control and post volumetric reduction at 15 watts initially with a 13% volumetric reduction, and 15 watts for 4 hours with an additional 4% volumetric reduction. A total 17% volumetric reduction was achieved.

EXAMPLE 2

Ablation apparatus 10 was used to determine three-dimensional shrinkage of a bovine tongue. RF volumetric reduction was achieved with a single needle electrode with eight miniature ultrasonic crystals, creating a cube. Application of 16 watts initially produced a 17% volumetric reduction of the tongue, 25 watts applied initially produced a 25% volumetric reduction, and 25 watts after hours produced an additional 4% reduction, for a total volumetric reduction of 29%.

EXAMPLE 3

A 35% volumetric reduction was achieved in porcine tongue in vivo, with three dimensional gross at 20 watts initial application.

Figure 19:
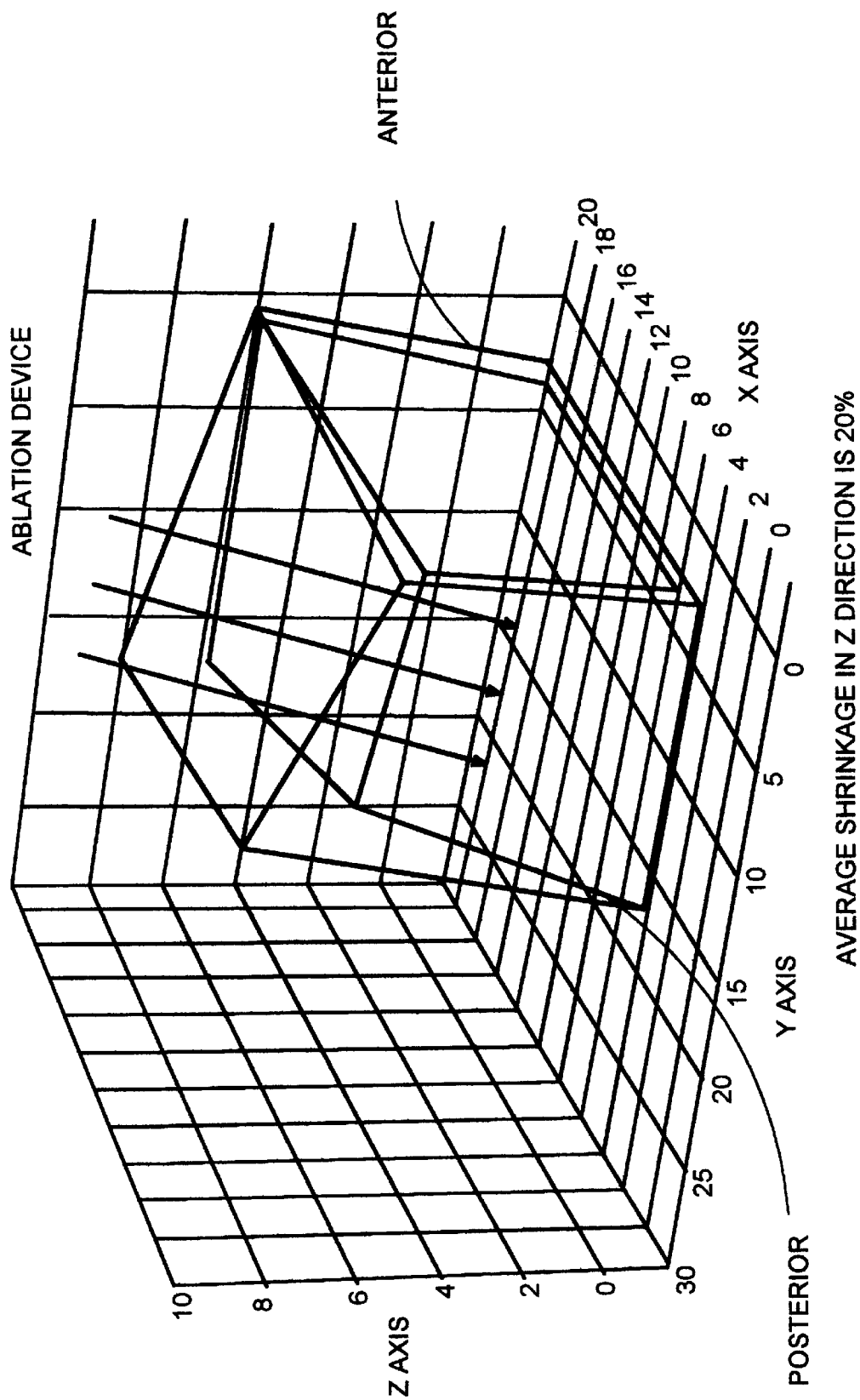
FIG. 19 is a three dimensional graph illustrating the percent shrinkage of the tongue following RF ablation.

Referring now to FIG. 19, ablation volume dimensions were measured with a multidimensional digital sonomicrometry. An average decrease in the Z direction was 20%, and volume shrinkage was 26%. Three-dimensional shrinkage of tongue tissue due to in vivo RF ablation with the needle, ablation with 20 Watts) is presented in FIG. 20. Control volume before ablation is compared with a post-ablation volume.

Figure 20:
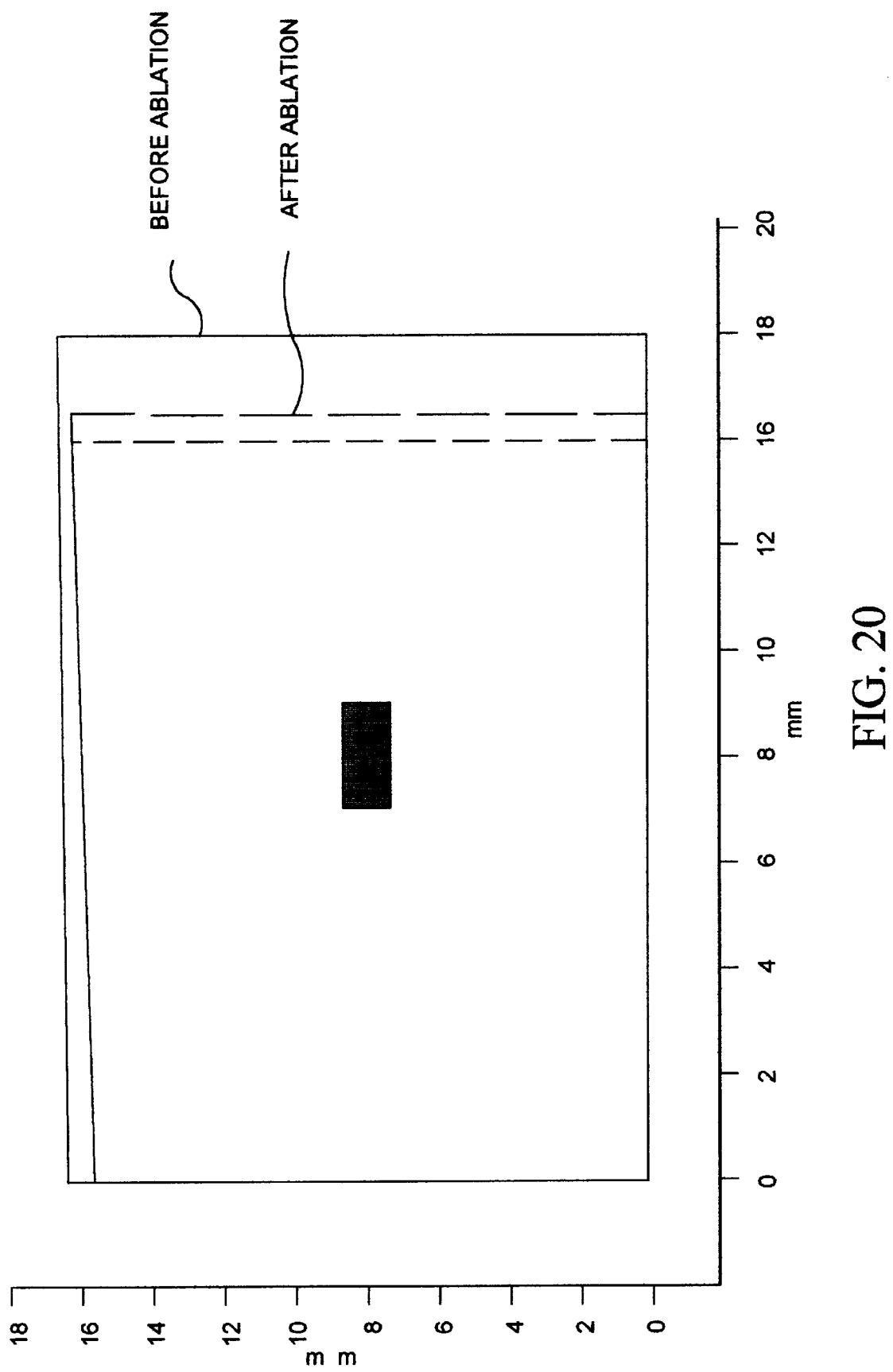
FIG. 20 is a graph illustrating two-dimensional shrinkage of bovine tongue tissue with RF ablation.

FIG. 20 illustrates two-dimensional shrinkage of a bovine tongue tissue due to RF ablation with a needle electrode. The before and after ablation results are illustrated.

Figure 21:
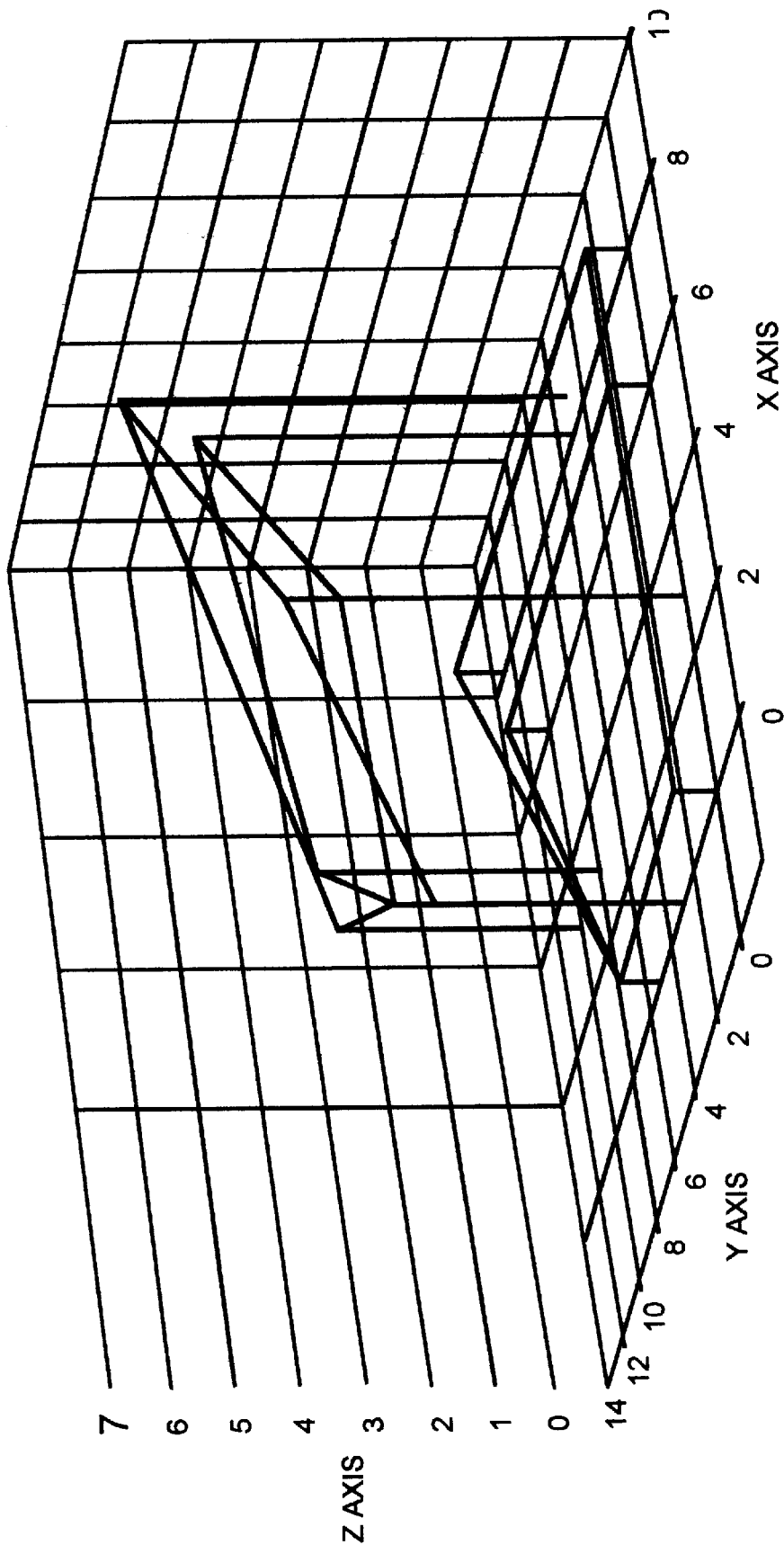
FIG. 21 is a graph illustrating three-dimensional shrinkage of bovine tongue tissue due to RF ablation.

FIG. 21 illustrates in graph form ablation at 16 Watts resulted in a 17% volume shrinkage of the tissue in post-ablation versus control. Ablation at 25 watts resulted in a 25% volume shrinkage after ablation. An additional 4% area shrinkage was obtained after in long-term post ablation (4 hours) versus post-ablation.

Figure 22:
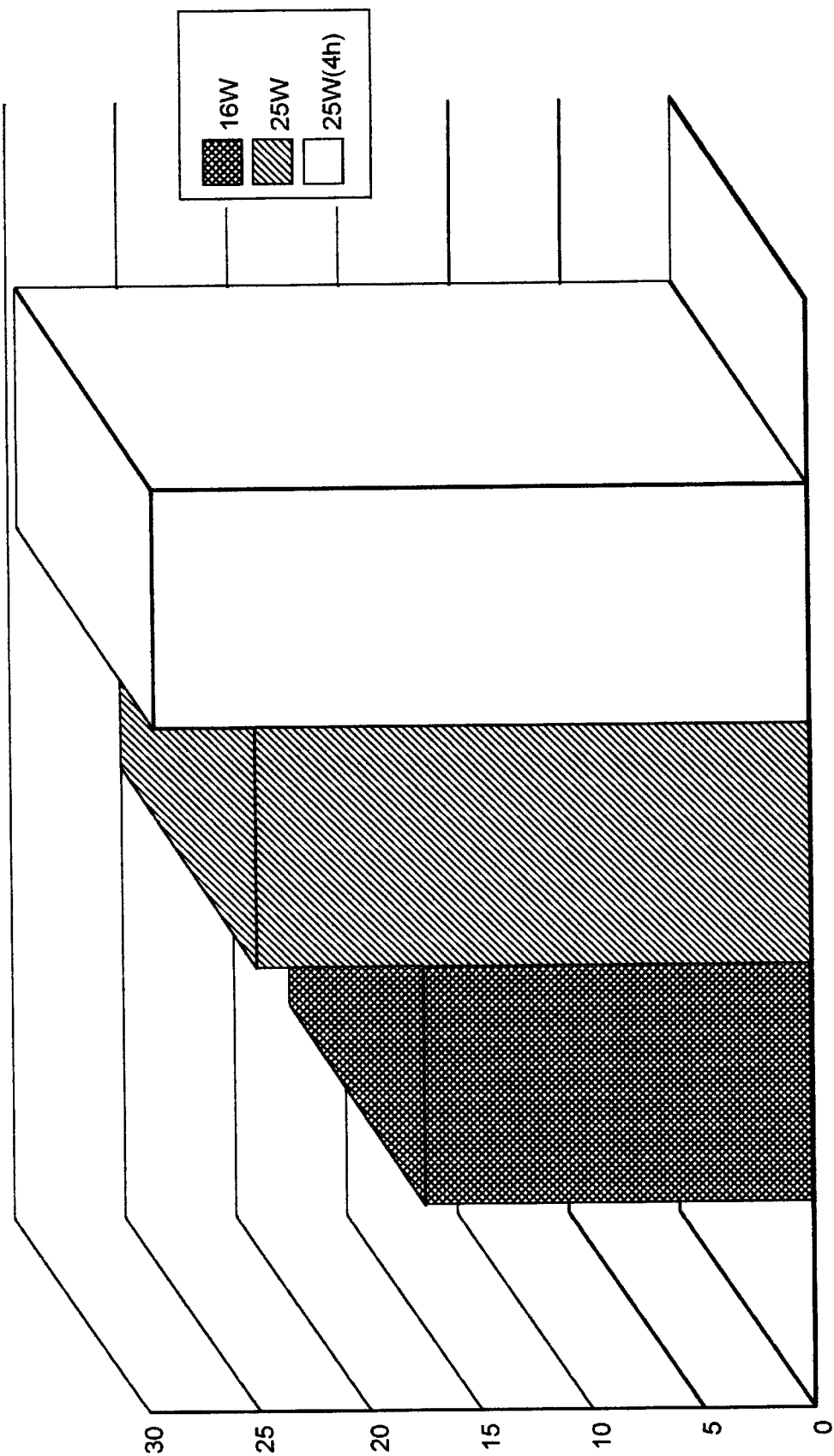
FIG. 22 is a graph illustrating percent volume change in a tongue following RF ablation.

FIG. 22 illustrates a percent volume change after RF ablation. 16 Watts, ablation at 16 Watts for 20 minutes; 25 Watts, ablation at 25 Watts for 20 minutes; 25 Watts (4 hours), and long tern post ablation (4 hours after 25 Watts ablation).

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An apparatus to reduce a volume of a selected site in an interior of the tongue, comprising:

a handpiece including a handpiece tongue interface surface;

an energy delivery device at least partially positioned in the interior of the handpiece, the energy delivery device including a tissue piercing energy delivery surface, the energy delivery surface being advanceable from the interior of the handpiece into the interior of the tongue;

an energy delivery device advancement member coupled to the energy delivery device and configured to advance the energy delivery device an advancement distance in the interior of the tongue, wherein the advancement distance is sufficient for the energy delivery surface to deliver energy to the selected tissue site and reduce a volume of the selected site without damaging a main branch of the hypoglossal nerve, wherein the advancement member advances at least a portion of the energy delivery device through the handpiece tongue interface surface in a lateral direction relative to a longitudinal axis of the handpiece; and a cable coupled to the energy delivery device.

2. The apparatus of claim 1, further comprising:

a temperature control device at least partially positioned in the interior of the handpiece and configured to cool a surface of the tongue.

3. The apparatus of claim 1, further comprising:

an insulator at least partially positioned around an exterior of the energy delivery device.

4. The apparatus of claim 3, further comprising:

a sensor positioned at a distal end of the insulator.

5. The apparatus of claim 1, further comprising:

a sensor positioned at a distal end of the energy delivery device.

6. The apparatus of claim 1, further comprising:

a sensor positioned on an exterior of the handpiece.

7. The apparatus of claim 1, further comprising:

a first sensor positioned at a distal end of the energy delivery device and a second sensor positioned at a distal end of an insulator, wherein the insulator is at least partially positioned around an exterior of the energy delivery device.

8. The apparatus of claim 1, further comprising:

an infusion medium source coupled to the energy delivery device.

9. An apparatus to reduce a volume of a selected site in an interior of the tongue, comprising:

a handpiece including a handpiece tongue interface surface;

an energy delivery device at least partially positioned in the interior of the handpiece, the energy delivery device including a tissue piercing energy delivery surface, the energy delivery device being advanceable from the interior of the handpiece into the interior of the tongue;

an energy delivery device advancement and retraction member coupled to the energy delivery device and configured to advance at least a portion of the energy delivery device to a placement position in the interior of the tongue, wherein at the placement position the energy delivery surface delivers sufficient energy to reduce a volume of the selected site without damaging a main branch of the hypoglossal nerve, wherein the advancement and retraction member advances at least a portion of the energy delivery device through the handpiece tongue interface surface in a lateral direction relative to a longitudinal axis of the handpiece; and a cable coupled to the energy delivery device.

10. The apparatus of claim 9, wherein the energy delivery device advancement and retraction member further comprises:

a guide channel configured to receive the energy delivery device in at least a portion of the interior of the handpiece and configured to guide an advancement direction of the energy delivery device from the handpiece into the interior of the tongue.

11. The apparatus of claim 9, wherein the electrode is an RF electrode.

12. The apparatus of claim 10, further comprising:

an RF energy source coupled to the RF electrode.

13. The apparatus of claim 9, further comprising:

a temperature control device at least partially positioned in the interior of the handpiece and configured to cool a surface of the tongue.

14. The apparatus of claim 9, further comprising:

an insulator at least partially positioned around an exterior of the energy delivery device.

15. The apparatus of claim 14, further comprising:

a sensor positioned at a distal end of the insulator.

16. The apparatus of claim 9, further comprising:

a sensor positioned at a distal end of the energy delivery device.

17. The apparatus of claim 9, further comprising:

a sensor positioned on an exterior of the handpiece.

18. The apparatus of claim 9, further comprising:

a first sensor positioned at a distal end of the energy delivery device and a second sensor positioned at a distal end of an insulator, wherein the insulator is at least partially positioned around an exterior of the energy delivery device.

19. The apparatus of claim 9, further comprising:

a feedback control device coupled to the energy delivery device, a sensor and an energy source.

20. The apparatus of claim 9, further comprising:

an infusion medium source coupled to the energy delivery device.

21. An apparatus to reduce a volume of a selected site in an interior of the tongue, comprising:

a handpiece including a handpiece tongue interface surface;

an energy delivery device at least partially positioned in the interior of the handpiece, the energy delivery device including a tissue piercing energy delivery surface and has an energy delivery device advancement length extending from an exterior of the handpiece to the interior of the tongue, wherein the advancement length is sufficient to position the energy delivery device energy delivery surface at the selected site and deliver sufficient energy to reduce a volume of the selected tissue site without damaging a main branch of the hypoglossal nerve, wherein the advancement and retraction member advances at least a portion of the energy delivery device through the handpiece tongue interface surface in a lateral direction relative to a longitudinal axis of the handpiece;

an energy delivery device advancement and retraction member coupled to the energy delivery device and configured to advance and retract at least a portion of the energy delivery device; and a cable coupled to the energy delivery device.

22. The apparatus of claim 21, wherein the electrode is an RF electrode.

23. The apparatus of claim 27, further comprising:

an RF energy source coupled to the RF electrode.

24. The apparatus of claim 21, further comprising:

a temperature control device at least partially positioned in the interior of the handpiece and configured to cool a surface of the tongue.

25. The apparatus of claim 24, further comprising:

a flow rate control device coupled to the temperature control device and configured to control a cooling medium flow rate through the cooling device.

26. The apparatus of claim 21, further comprising:

an insulator at least partially positioned around an exterior of the energy delivery device.

27. The apparatus of claim 26, further comprising:

a sensor positioned at a distal end of the insulator.

28. The apparatus of claim 21, further comprising:

a sensor positioned at a distal end of the energy delivery device.

29. The apparatus of claim 21, further comprising:

a sensor positioned on an exterior of the handpiece.

30. The apparatus of claim 21, further comprising:

a first sensor positioned at a distal end of the energy delivery device and a second sensor positioned at a distal end of an insulator, wherein the insulator is at least partially positioned around an exterior of the energy delivery device.

31. The apparatus of claim 21, further comprising:

an infusion medium source coupled to the energy delivery device.

32. An apparatus to reduce a volume of a selected site in an interior of the tongue, comprising:

a handpiece including a handpiece tongue interface surface;

an energy delivery device at least partially positioned in the interior of the handpiece and advanceable from the interior of the handpiece into the interior of the tongue, wherein the energy delivery device has a tissue piercing energy delivery surface with a geometric shape configured to reduce a volume of the selected site without damaging a main branch of the hypoglossal nerve;

an energy delivery device advancement and retraction member coupled to the energy delivery device and configured to advance and retract at least a portion of the energy delivery device, wherein the advancement and retraction member advances at least a portion of the energy delivery device through the handpiece tongue interface surface in a lateral direction relative to a longitudinal axis of the handpiece; and a cable coupled to the energy delivery device.

33. The apparatus of claim 32, wherein the electrode is an RF electrode.

34. The apparatus of claim 33, further comprising:

an RF energy source coupled to the RF electrode.

35. The apparatus of claim 32, further comprising:

a temperature control device at least partially positioned in the interior of the handpiece and configured to cool a surface of the tongue.

36. The apparatus of claim 32, further comprising:

an insulator at least partially positioned around an exterior of the energy delivery device.

37. The apparatus of claim 36, further comprising:

a sensor positioned at a distal end of the insulator.

38. The apparatus of claim 32, further comprising:

a sensor positioned at a distal end of the energy delivery device.

39. The apparatus of claim 32, further comprising:

a sensor positioned on an exterior of the handpiece.

40. The apparatus of claim 32, further comprising:

a first sensor positioned at a distal end of the energy delivery device and a second sensor positioned at a distal end of an insulator, wherein the insulator is at least partially positioned around an exterior of the energy delivery device.

41. The apparatus of claim 32, further comprising:

an infusion medium source coupled to the energy delivery device.

42. An apparatus to reduce a volume of a selected site in an interior of the tongue, comprising:

a handpiece including a handpiece tongue interface surface; and an energy delivery device at least partially positioned in the interior of the handpiece, the energy delivery device including a tissue penetrating energy delivery device surface and having an energy delivery device advancement length extending from an exterior of the handpiece to the interior of the tongue, wherein the advancement length is sufficient to position the energy delivery surface at the selected site and deliver sufficient energy to reduce a volume of the selected tissue site without damaging a main branch of the hypoglossal nerve, wherein at least a portion of the energy delivery device extends from the handpiece tongue interface surface in a lateral direction relative to a longitudinal axis of the handpiece.

* * * * *